United States Patent
Liang et al.

(10) Patent No.: US 12,016,921 B2
(45) Date of Patent: Jun. 25, 2024

(54) METHODS FOR TREATMENT OF PSORIASIS WITH AN ANTI-APO B100 ANTIBODY

(71) Applicant: Abcentra, LLC, Los Angeles, CA (US)

(72) Inventors: Bertrand C. Liang, San Diego, CA (US); Stacey Ruiz, Beverly Hills, CA (US); Christopher John Farina, Los Angeles, CA (US)

(73) Assignee: Abcentra, LLC, Los Angeles, CA (US)

( * ) Notice: Subject to any disclaimer, the term of this patent is extended or adjusted under 35 U.S.C. 154(b) by 625 days.

(21) Appl. No.: 17/058,537

(22) PCT Filed: May 29, 2019

(86) PCT No.: PCT/US2019/034423
§ 371 (c)(1),
(2) Date: Nov. 24, 2020

(87) PCT Pub. No.: WO2019/232070
PCT Pub. Date: Dec. 5, 2019

(65) Prior Publication Data
US 2021/0205448 A1 Jul. 8, 2021

Related U.S. Application Data

(60) Provisional application No. 62/677,590, filed on May 29, 2018.

(51) Int. Cl.
| | | |
|---|---|---|
| A61P 17/06 | (2006.01) | |
| A61K 39/395 | (2006.01) | |
| C07K 16/18 | (2006.01) | |
| A61K 9/00 | (2006.01) | |
| A61K 31/203 | (2006.01) | |
| A61K 31/573 | (2006.01) | |
| A61K 31/593 | (2006.01) | |
| A61K 35/04 | (2006.01) | |
| A61K 39/00 | (2006.01) | |
| A61K 45/06 | (2006.01) | |
| C07K 14/775 | (2006.01) | |

(52) U.S. Cl.
CPC .......... *A61K 39/3955* (2013.01); *A61P 17/06* (2018.01); *C07K 16/18* (2013.01); *A61K 9/0019* (2013.01); *A61K 31/203* (2013.01); *A61K 31/573* (2013.01); *A61K 31/593* (2013.01); *A61K 35/04* (2013.01); *A61K 2039/505* (2013.01); *A61K 2039/54* (2013.01); *A61K 2039/545* (2013.01); *A61K 45/06* (2013.01); *C07K 14/775* (2013.01); *C07K 2317/51* (2013.01); *C07K 2317/515* (2013.01); *C07K 2317/56* (2013.01); *C07K 2317/565* (2013.01)

(58) Field of Classification Search
CPC .. C07K 16/18; C07K 14/755; A61K 39/3955; A61P 17/06
See application file for complete search history.

(56) References Cited

U.S. PATENT DOCUMENTS

| | | |
|---|---|---|
| 2010/0028363 A1 | 2/2010 | Valdes et al. |
| 2010/0286025 A1 | 11/2010 | Anantharamaiah et al. |

FOREIGN PATENT DOCUMENTS

| | | |
|---|---|---|
| WO | WO-02/080954 A1 | 10/2002 |
| WO | WO-2008/104194 A1 | 9/2008 |
| WO | WO-2011/025978 A2 | 3/2011 |
| WO | WO-2016/024254 A1 | 2/2016 |
| WO | WO-2019/232081 A1 | 12/2019 |

OTHER PUBLICATIONS

Armstrong et al., "A tale of two plaques: convergent mechanisms of T-cell-mediated inflammation in psoriasis and atherosclerosis," Exp Dermatol. 20(7):544-49 (2011).
Fotiadou et al., "Management of psoriasis in adolescence," Adolesc Health Med Ther. 14(5):25-34 (2014).
International Preliminary Report on Patentability for International Application No. PCT/US2019/034423, dated Dec. 1, 2020 (10 pages).
Pietrzak et al., "Serum lipid metabolism in psoriasis and psoriatic arthritis—an update," Arch Med Sci. 15(2):369-375 (2019).
Takahashi et al., "Psoriasis and metabolic syndrome," J Dermatol. 39(3):212-8 (2012).
Uyanik et al., "Serum lipids and apolipoproteins in patients with psoriasis," Clin Chem Lab Med. 40(1):65-8 (2002).
Extended European Seach Report for European Patent Application No. 19811281.5, dated Feb. 10, 2022 (13 pages).

*Primary Examiner* — Zachary C Howard
(74) *Attorney, Agent, or Firm* — Clark & Elbing LLP

(57) ABSTRACT

Compositions and methods for treating a subject with psoriasis are provided, including an inhibitor of oxidized low density lipoprotein (LDL), malondialdehyde-modified epitope in LDL or native LDL for administration. Exemplary inhibitors of oxidized or malondialdehyde-modified LDL include orticumab, a variant antibody or peptides capable of binding oxidized or malondialdehyde-modified LDL, which results in improvement in conditions of psoriasis even in patients that are refractory to ultraviolet A/B therapy and topical steroids.

20 Claims, 4 Drawing Sheets
Specification includes a Sequence Listing.

SEQUENCE LISTING

```
<160> NUMBER OF SEQ ID NOS: 11

<210> SEQ ID NO 1
<211> LENGTH: 20
<212> TYPE: PRT
<213> ORGANISM: Artificial Sequence
<220> FEATURE:
<223> OTHER INFORMATION: P45 of apoB100

<400> SEQUENCE: 1

Ile Glu Ile Gly Leu Glu Gly Lys Gly Phe Glu Pro Thr Leu Glu Ala
1               5                   10                  15

Leu Phe Gly Lys
            20

<210> SEQ ID NO 2
<211> LENGTH: 14
<212> TYPE: PRT
<213> ORGANISM: Artificial Sequence
<220> FEATURE:
<223> OTHER INFORMATION: HCDR1

<400> SEQUENCE: 2

Phe Ser Asn Ala Trp Met Ser Trp Val Arg Gln Ala Pro Gly
1               5                   10

<210> SEQ ID NO 3
<211> LENGTH: 19
<212> TYPE: PRT
<213> ORGANISM: Artificial Sequence
<220> FEATURE:
<223> OTHER INFORMATION: HCDR2

<400> SEQUENCE: 3

Ser Ser Ile Ser Val Gly Gly His Arg Thr Tyr Tyr Ala Asp Ser Val
1               5                   10                  15

Lys Gly Arg

<210> SEQ ID NO 4
<211> LENGTH: 14
<212> TYPE: PRT
<213> ORGANISM: Artificial Sequence
<220> FEATURE:
<223> OTHER INFORMATION: HCDR3

<400> SEQUENCE: 4

Ala Arg Ile Arg Val Gly Pro Ser Gly Gly Ala Phe Asp Tyr
1               5                   10

<210> SEQ ID NO 5
<211> LENGTH: 14
```

```
<212> TYPE: PRT
<213> ORGANISM: Artificial Sequence
<220> FEATURE:
<223> OTHER INFORMATION: LCDR1

<400> SEQUENCE: 5

Cys Ser Gly Ser Asn Thr Asn Ile Gly Lys Asn Tyr Val Ser
1               5                   10

<210> SEQ ID NO 6
<211> LENGTH: 7
<212> TYPE: PRT
<213> ORGANISM: Artificial Sequence
<220> FEATURE:
<223> OTHER INFORMATION: LCDR2

<400> SEQUENCE: 6

Ala Asn Ser Asn Arg Pro Ser
1               5

<210> SEQ ID NO 7
<211> LENGTH: 12
<212> TYPE: PRT
<213> ORGANISM: Artificial Sequence
<220> FEATURE:
<223> OTHER INFORMATION: LCDR3

<400> SEQUENCE: 7

Cys Ala Ser Trp Asp Ala Ser Leu Asn Gly Trp Val
1               5                   10

<210> SEQ ID NO 8
<211> LENGTH: 120
<212> TYPE: PRT
<213> ORGANISM: Artificial Sequence
<220> FEATURE:
<223> OTHER INFORMATION: Variable heavy region

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ser Ile Ser Val Gly Gly His Arg Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Val Gly Pro Ser Gly Gly Ala Phe Asp Tyr Trp Gly
            100                 105                 110

Gln Gly Thr Leu Val Thr Val Ser
        115                 120

<210> SEQ ID NO 9
<211> LENGTH: 110
<212> TYPE: PRT
<213> ORGANISM: Artificial Sequence
<220> FEATURE:
<223> OTHER INFORMATION: Variable light region

<400> SEQUENCE: 9
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Asn Thr Asn Ile Gly Lys Asn
            20                  25                  30

Tyr Val Ser Trp Tyr Gln Gln Leu Pro Gly Thr Ala Pro Lys Leu Leu
        35                  40                  45

Ile Tyr Ala Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
                85                  90                  95

Asn Gly Trp Val Phe Gly Gly Gly Thr Lys Leu Thr Val Leu
            100                 105                 110

<210> SEQ ID NO 10
<211> LENGTH: 451
<212> TYPE: PRT
<213> ORGANISM: Artificial Sequence
<220> FEATURE:
<223> OTHER INFORMATION: Heavy chain

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ser Ile Ser Val Gly Gly His Arg Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Val Gly Pro Ser Gly Ala Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

-continued

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 11
<211> LENGTH: 216
<212> TYPE: PRT
<213> ORGANISM: Artificial Sequence
<220> FEATURE:
<223> OTHER INFORMATION: Light chain

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Asn Thr Asn Ile Gly Lys Asn
            20                  25                  30

Tyr Val Ser Trp Tyr Gln Gln Leu Pro Gly Thr Ala Pro Lys Leu Leu
        35                  40                  45

Ile Tyr Ala Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

METHODS FOR TREATMENT OF PSORIASIS WITH AN ANTI-APO B100 ANTIBODY

CROSS-REFERENCE TO RELATED APPLICATIONS

This application includes a claim of priority under 35 U.S.C. § 119(e) to U.S. provisional patent application No. 62/677,590, filed May 29, 2018, the entirety of which is hereby incorporated by reference.

FIELD OF INVENTION

This invention relates to the treatment of psoriasis in a patient and the treatment of atherosclerosis in patients with psoriasis.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Psoriasis is a chronic inflammatory disease that manifests as scaly patches of skin, which occurs due to hyperproliferation of keratinocytes and activated immune cells. Treatment typically involves immune mediation, such as the use of anti-inflammatory agents including topical corticosteroids, ultraviolet (UV) A and B light therapy, or cytotoxic agents. In patients who are refractory to topical treatment and/or UVA/B therapy, anti-inflammatory biologic therapies are initiated, such as monoclonal antibodies against TNFα, IL-12/23, and IL-17 or antibodies against IL-23 only.

Many systemic treatments for psoriasis have adverse cardiovascular effects, such as dyslipidemia and hypertension. The highly oxidative environment produced by psoriatic inflammation promotes oxidation of LDL and endothelial dysfunction, two key contributors to atherosclerosis development.

Oxidized LDL (oxLDL) forms when LDL infiltrates the subendothelial space in the arterial wall and comes into contact with reactive oxygen species, which are highly upregulated in psoriasis. Through the process of LDL oxidation, various adducts (e.g., malondialdehyde [MDA]) are formed, which further modify LDL (i.e., MDA-LDL). The oxidized/modified LDL acts in a myriad of ways supporting inflammation and atherosclerosis. Without being bound by any theory, such molecules affect the proliferation and migration of vascular smooth muscle cells (VSMCs) likely through binding to lectin-type oxidized LDL receptor 1 (LOX-1), which are pivotal events in atherosclerotic plaque progression. The oxidized/modified LDL is also taken up by macrophages, which become foam cells and stimulate a pro-inflammatory response that results in both the build-up of a necrotic core in the vessel plaque and recruitment of additional monocytes to the plaque. This process provides a feed-forward loop of chronic inflammation that contributes to plaque growth, as well as plaque instability. Elevated levels of oxLDL and MDA-LDL, as well as LOX-1, have been found both in the plaque and plasma of patients at risk for developing CVD and inflammation.

Therefore, it is an objective of the present invention to provide compositions for use in and methods for treating, reducing the severity or likelihood of psoriasis in a subject.

SUMMARY OF THE INVENTION

The following embodiments and aspects thereof are described and illustrated in conjunction with compositions and methods which are meant to be exemplary and illustrative, not limiting in scope.

Methods for treating, reducing the severity of, slowing progression of or inhibiting psoriasis in a subject in need thereof are provided, which include administering to the subject an effective amount of an antibody or antibody fragment capable of binding to a fragment of apolipoprotein B100 (ApoB100), wherein the fragment of ApoB100 comprises an amino acid sequence of SEQ ID No.: 1 or an active site thereof, and wherein the antibody comprises one, two or three heavy chain complementarity determining regions (HCDRs) selected from the group consisting of HCDR 1 (HCDR1), HCDR 2 (HCDR2) and HCDR 3 (HCDR3) sequences of SEQ ID Nos: 2, 3 and 4, respectively, and one, two or three light chain complementarity determining regions (LCDRs) selected from the group consisting of LCDR 1 (LCDR1), LCDR 2 (LCDR2) and LCDR 3 (LCDR3) sequences of SEQ ID Nos: 5, 6 and 7, respectively.

Further embodiments provide that the method of treating, reducing the severity or likelihood of psoriasis includes administering one or more therapeutic agents or therapies in combination (e.g., sequentially or concurrently) with an antibody or antibody fragment that binds an epitope of SEQ ID No.:1 of ApoB100. Exemplary additional therapeutic agents or therapies to the inhibitors of oxLDL or of malondialdehyde-modified LDL include corticosteroids, ultraviolet (UV) A therapy, UV B therapy, anti-TNFα antibodies, anti-IL-12/23 antibodies or an anti-IL-23 antibody which only binds IL-23 alone, and anti-IL-17 antibodies. In other embodiments, the composition does not include these additional therapeutic agents or therapies.

The subject can be diagnosed with psoriasis as characterized by an elevated amount of tumor necrosis factor-alpha (TNFα), interleukin 6 (IL-6), C-reactive protein (CRP), or a combination thereof, compared to a control subject free of psoriasis. In other aspects, the subject is diagnosed with plaque psoriasis and does not have or show symptoms of non-plaque psoriasis.

Various embodiments of the disclosed methods include administering subcutaneously an antibody (e.g., orticumab) or antibody fragment at about 330 mg per period of about a monthly interval to an adult human subject to treat psoriasis or provide passive immunity.

Other embodiments provide administering an effective amount of an anti-LDL or an anti-oxLDL antibody in the method described herein at an initial dose in an amount of at least 5 mg/kg, or preferably at least 8 mg/kg. In some embodiments, an initial dose is sufficient to result in improvement and treatment of psoriasis in a patient. In further embodiments, the methods further include administering a plurality of subsequent doses of the composition in an amount that is at least about 2 mg/kg/week, at least about 2.5 mg/kg/two weeks, or at least about 6 mg/kg/month. Typically, an effective amount of an anti-LDL antibody or an anti-oxLDL antibody in the described method results in an antibody amount of at least 4 µg/mL in circulation, preferably at least 12 µg/mL in circulation; an effective amount of an anti-LDL antibody or an anti-oxLDL antibody includes a plurality of doses resulting in an antibody amount of at least 4 µg/mL in circulation, preferably at least 12 µg/mL in circulation for an extended period of time (e.g., at least 30 minutes, 1 hour, 2 hours, 3 hours, 4 hours, 1 day, 2 days, 3 days, 1 week, 2 weeks, 3 weeks, 1 month, 2 months or 3 months). In some aspects, the amount in each of the subsequent doses is approximately the same or less than the initial dose, where the subsequent doses are separated in time from each other by at least 3 days, 5 days, 7 days, 2 weeks, 3 weeks, or 1 month.

Another exemplary embodiment provides administering step-wise escalating doses of an antibody against native or oxidized LDL to treat psoriasis. In this embodiment, an exemplary (starting) dose of a single-dose administration of an antibody (e.g., orticumab) against native or oxidized LDL is between 0.005 and 0.01 mg/kg (e.g., intravenously); and other exemplary dosage levels to be administered in the single-dose administration are between 0.01 and 0.15, between 0.15 and 0.75, between 0.75 and 2.5, between 2.5 and 7.5, and between 7.5 and 30 mg/kg (e.g., intravenously). For example, a starting dose of orticumab in a single-dose intravenous administration is 0.007 mg/kg; and other exemplary dosages can be 0.05, 0.25, 1.25, 5.0 or 15.0 mg/kg in subsequent single-dose intravenous administration. In another embodiment, a single-dose subcutaneous administration of an antibody against native or oxidized LDL is between 0.5 and 6 mg/kg, and a multiple-dose subcutaneous administration is also between 0.5 and 6 mg/kg. For example, an antibody against native or oxidized LDL at 1.25 mg/kg is administered subcutaneously. In various embodiments, the dosage is administered within a specified hour range of the day in each administration, and each dose in a multiple-dose treatment (e.g., 4 doses, 3 doses, 5 doses, or 6 doses) is administered at weekly intervals with a time window of ±1 day. In another example, an antibody (such as orticumab) against native or oxidized LDL is administered at between 300 mg and 450 mg (e.g., 360 mg) to a human subject, optionally followed by another dose between 300 mg and 450 mg (e.g., 360 mg) to the human subject where the second dose is at least 70 days (up to 91 days) apart from the first dose. The antibody (such as orticumab) may be formulated at a concentration of 100-170 mg/mL (e.g., 150 mg/mL) and for use in subcutaneous administration without further dilution, or diluted to a large volume for intravenous infusion.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

In FIG. 2A, the highest solid line between 0 and 96 hours indicates dosing at a weekly frequency at 2 mg/kg; generally the middle solid line between 24 and 96 hours indicates dosing at a bi-weekly frequency at 2 mg/kg; and generally the lowest solid line indicates dosing at a monthly frequency at 2 mg/kg. In FIG. 2B, the solid line indicates a loading dose at 5 mg/kg and subsequent doses at 2 mg/kg every two weeks. Generally lower dashed line indicates a desired threshold of 4 µg/mL of the serum concentration of orticumab. Generally higher dashed line indicates a desired threshold of 12 µg/mL of the serum concentration of orticumab.

DESCRIPTION OF THE INVENTION

Figure 1:
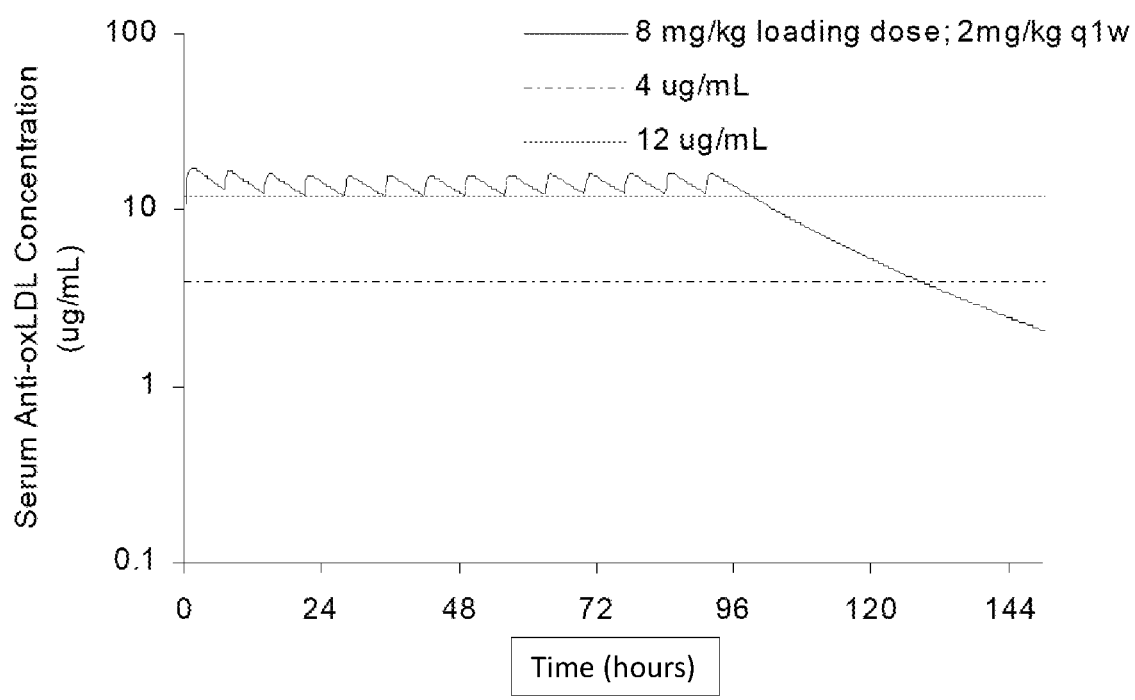
FIG. 1 depicts a simulated human pharmacokinetics (PK) profile after a subcutaneous (SC) loading dose of 8 mg/kg followed by a weekly SC dosing of 2 mg/kg (the solid line). Dashed lines indicate two desired thresholds (4 µg/mL, generally lowest line, and 12 µg/mL, the higher dashed line) of the serum concentration of orticumab.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., Revised, J. Wiley & Sons (New York, NY 2006); March, *Advanced Organic Chemistry Reactions, Mechanisms and Structure* $7^{th}$ ed., J. Wiley & Sons (New York, NY 2013); and Sambrook and Russel, *Molecular Cloning: A Laboratory Manual* $4^{th}$ ed., Cold Spring Harbor Laboratory Press (Cold Spring Harbor, NY 2012), provide one skilled in the art with a general guide to many of the terms used in the present application. For references on how to prepare antibodies, see D. Lane, *Antibodies: A Laboratory Manual* $2^{nd}$ ed. (Cold Spring Harbor Press, Cold Spring Harbor NY, 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334:544-54 (1989); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "antibody" or "antibodies" as used herein are meant in a broad sense and includes immunoglobulin molecules including polyclonal antibodies, monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (x) and lambda (k), based on the amino acid sequences of their constant domains.

The term "antibody fragment" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region ($V_H$), or a light chain variable region ($V_L$). Antibody fragments include a Fab fragment, a monovalent fragment consisting of the $V_L$, $V_H$, $C_L$ and $C_{H1}$ domains; a F(ab)$_2$ fragment, a bivalent fragment comprising two Fab fragments linked by a disulfide bridge at the hinge region; a Fd fragment consisting of the $V_H$ and $C_{H1}$ domains; a Fv fragment consisting of the $V_L$ and $V_H$ domains of a single arm of an antibody; a domain antibody (dAb) fragment (Ward et al (1989) Nature 341:544-546), which consists of a $V_H$ domain. $V_H$ and $V_L$ domains can be engineered and linked together via a synthetic linker to form various types of single chain antibody designs where the $V_H/V_L$ domains pair intramolecularly, or intermolecularly in those cases when the $V_H$ and $V_L$ domains are expressed by separate single chain antibody constructs, to form a monovalent antigen binding site, such as single chain Fv (scFv) or diabody; described for example in PCT Intl. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

An antibody variable region consists of a "framework" region interrupted by three "antigen binding sites". The antigen binding sites are defined using various terms such as Complementarity Determining Regions (CDRs), three in the $V_H$ (HCDR1, HCDR2, HCDR3), and three in the $V_L$ (LCDR1, LCDR2, LCDR3), are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991) or "Hypervariable regions", "HVR", or "HV", three in the $V_H$ (H1, H2, H3) and three in the $V_L$ (L1, L2, L3), refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database provides a standardized numbering and definition of antigen-binding sites. The correspondence between CDRs, HVs and IMGT delineations is described in Lefranc et al., Dev Comparat Immunol 27:55-77, 2003.

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Humanized antibody" refers to an antibody in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human-adapted" antibodies or "human framework adapted (HFA)" antibodies refer to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy or light chain variable regions that are "derived from" sequences of human origin wherein the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. A "human antibody" may contain amino acid differences when compared to the human germline or rearranged immunoglobulin sequences due to for example naturally occurring somatic mutations or intentional introduction of substitutions in the framework or antigen binding sites. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, "human antibody" may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462. Antibodies in which antigen binding sites are derived from a non-human species are not included in the definition of human antibody.

The term "recombinant antibody" as used herein, includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom (described further below), antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

The term "monoclonal antibody" as used herein refers to a preparation of antibody molecules of single molecular composition. A monoclonal antibody composition displays a single binding specificity and affinity for a particular epitope, or in a case of a bispecific monoclonal antibody, a dual binding specificity to two distinct epitopes.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" as used herein refers to a polypeptide or a polynucleotide that differs from a reference polypeptide or a reference polynucleotide by one or more modifications for example, substitutions, insertions or deletions.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, sub arachnoid, subcapsular, subcutaneous, transmucosal, or transtracheal. Via the parenteral route, the compositions may be in the form of solutions or suspensions for infusion or for injection, or as lyophilized powders.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and/or prolonging a patient's life or life expectancy. In some embodiments, the disease condition is psoriasis, or a combination of psoriasis and atherosclerosis.

The term "effective amount" as used herein refers to the amount of a pharmaceutical composition to decrease at least one or more symptom of the disease or disorder, and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment. In various embodiments, the pharmaceutical compositions described herein further comprise a pharmaceutically acceptable carrier. In some embodiments, a therapeutic pharmaceutical composition is used, for example, to treat, inhibit, reduce the severity of and/or, reduce duration of psoriasis, or a combination of psoriasis and atherosclerosis, and/or related symptoms in a subject in need thereof.

A therapeutically or prophylactically significant reduction in a symptom is, e.g. at least 5%, at least 10%, at least 20%, at least 30%, at least 40%, at least 50%, at least 60%, at least 70%, at least 80%, at least 90%, at least 100%, or more in a measured parameter as compared to a control or non-treated subject or the state of the subject prior to administering the compositions described herein. Measured or measurable parameters include clinically detectable markers of disease, for example, elevated or depressed levels of a biological marker, as well as parameters related to a clinically accepted scale of symptoms or markers for psoriasis and/or atherosclerosis. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject. "Ineffective" treatment refers to when a subject is administered a treatment and there is less than 1%, 2%, 3%, 4% or 5%, improvement in symptoms.

"Subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease-state is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented. For example, Example 3 sets forth embodiments of measuring treatment efficacy, e.g., improvement on the symptoms. In one aspect, a reduction in the Psoriasis Area and Severity Index (PAST) score from baseline indicates improvement. In another aspect, a two-point improvement in the 5-point Investigator Global Assessment (IGA) scale compared to baseline, and reaching to a point of designation 'clear' or 'almost clear' indicates improvement.

The term "statistically significant" or "significantly" refers to statistical evidence that there is a difference. It is defined as the probability of making a decision to reject the null hypothesis when the null hypothesis is actually true. The decision is often made using the p-value.

A "cardiovascular disease," as used herein, refers to a disorder of the heart and blood vessels, and includes disorders of the arteries, veins, arterioles, venules, and capillaries. Non-limiting examples of cardiovascular diseases include congestive heart failure, arrhythmia, pericarditis, acute myocardial infarction, infarcted myocardium, coronary artery disease, coronary heart disease, ischemic heart disease, cardiomyopathy, stroke, hypertensive heart disease, heart failure, pulmonary heart disease, ischemic syndrome, coronary microvascular disease, cardiac dysrhythmias, rheumatic heart disease, aortic aneurysms, atrial fibrillation, congenital heart disease, endocarditis, inflammatory heart disease, endocarditis, inflammatory cardiomegaly, myocarditis, valvular heart disease, cerebrovascular disease, and peripheral artery disease, or any combination thereof.

"Psoriasis" refers to an immune-mediated disease that causes raised, red, scaly patches to appear on the skin. As a skin condition, psoriasis speeds up the life cycle of skin cells, causing cells to build up rapidly on the surface of the skin and sometimes itchy and painful. Psoriasis can have different types. For example, plaque psoriasis (or psoriasis vulgaris) is a common form of the disease and appears as raised, red patches covered with a silvery white buildup of dead skin cells or scale. These patches or plaques often appear on the scalp, knees, elbows and lower back. Another form is guttate psoriasis, which appears in small red spots on the skin, often on the torso and limbs but can also appear on face and scalp. The spots are usually not as thick as plaque psoriasis, but can develop into plaque psoriasis over time. Flexural or inverse psoriasis is another form of psoriasis, which often appears in skinfolds, such as under the breasts or in the armpits or groin area. This type of psoriasis is red and often shiny and smooth. The sweat and moisture from skinfolds keeps this form of psoriasis from shedding skin scales. Pustular psoriasis is a severe form of psoriasis, which develops fast in the form of many white pustules surrounded by red skin. Three kinds of pustular psoriasis, i.e., von Zumbusch, palmoplantar pustulosis, and acropustulosis, can have different symptoms and severity. Additionally, erythrodermic psoriasis, or exfoliative psoriasis, is a rare psoriasis type that looks like severe burns. This form of psoriasis is widespread, red, and scaly. This serious condition may result in the sufferer not able to control body temperature.

"Psoriatic arthritis" is a form of inflammatory arthritis that affects some people who have psoriasis—a condition that features red patches of skin topped with silvery scales. For psoriatic arthritis, most people develop psoriasis first and are later diagnosed with psoriatic arthritis, but the joint problems can sometimes begin before skin lesions appear.

"Bind" in reference to the interaction between antibody and epitope, "selectively binds" or "specifically binds" refers to the ability of an antibody or antibody fragment thereof described herein to bind to a target, such as a molecule present on the cell-surface, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

The term "in combination with" as used herein means that two or more therapeutics can be administered to a subject together in a mixture, concurrently as single agents or sequentially as single agents in any order.

Methods and Systems

Various embodiments provide a method of treating, reducing the severity of psoriasis by administering to the subject an antibody or antibody fragment that binds to at least one fragment of apolipoprotein B100 (apoB100). In various embodiments, the method provides treatment of psoriasis by passive immunization.

Various embodiments provide a method of reducing the likelihood of having psoriasis in a subject by administering to the subject an antibody or antibody fragment that binds to at least one fragment of apolipoprotein B100 (apoB100). In various embodiments, the method provides passive immunity to the subject to reduce the likelihood of having psoriasis.

Various embodiments provide the antibody or antibody fragment in the methods disclosed herein binds to a native and/or an oxidized epitope P45 of apoB100. Various embodiments provide the antibody or antibody fragment in the methods disclosed herein only binds to a native and/or an oxidized epitope P45 of apoB100. P45 of apoB100 has a polypeptide sequence of IEIGLEGKGFEPTLEALFGK (SEQ ID No.: 1). An oxidized epitope or oxidized lipoprotein includes but is not limited to a modification on the epitope or lipoprotein to carry malone-di-aldehyde (MDA) groups on lysines and histidines, a modification that is induced by oxidation by copper (e.g., CuOxLDL), a modification to carry hydroxynonenal, or a modification to carry a hapten of an aldehyde. Another embodiment provides the antibody or antibody fragment in the method disclosed herein further binds one or more fragments of apoB100.

ApoB100 contains peptide fragments that can be identified as P1-P302, which have overlapping amino acids between adjacent peptides, as described in U.S. patent application publication no. US/2017/0340702 and U.S. Pat. Nos. 7,468,183 and 7,704,499, which are incorporated by reference herein in their entireties.

Various embodiments provide that the method of treating or reducing the severity of psoriasis in a subject includes but is not limited to administering orticumab or a variant of orticumab that has identical heavy chain and/or light chain to those of orticumab, or identical complementarity determining regions to those of orticumab, which is also detailed below.

Various embodiments provide that the method of reducing the likelihood of psoriasis in a subject includes but is not limited to administering orticumab or a variant of orticumab that has identical heavy chain and/or light chain to those of orticumab, or identical complementarity determining regions to those of orticumab, which is also detailed below. In further aspect, the method provides passive immunity to the subject to reduce the likelihood of having psoriasis.

Various embodiments of the methods disclosed herein include that the subject after the treatment is clear or almost clear of psoriasis plaques, or has a ≥2-point improvement in psoriasis measurement according to one or more of the 5-point static Investigator's Global Assessment modified 2011 version (sIGA), the Physician's Global Assessment (PGA) scale, and the Pustular Symptom Score (PSS), compared to before the treatment.

Various embodiments provide the methods disclosed herein include that the subject after the treatment has reduced plaque areas in one or more of four body areas, namely the head and neck, the upper limbs, the trunk, and the lower limbs, compared to before the treatment. Other embodiments provide the methods disclosed herein include that the subject after the treatment has reduced psoriasis area and severity index (PAST). The PASI combines assessments of 4 body areas: the head and neck (H), the upper limbs (UL), the trunk (T) and the lower limbs (LL). The percentage of skin affected by psoriasis in each area is given a numerical score representing the Percentage involved: 1 (0-9%), 2 (10-29%), 3 (30-49%), 4 (50-69%), 5 (70-89%) or 6 (90-100%). Within each area (H, UL, T, LL) the severity of 3 plaque signs—erythema (E), thickness/induration (I) and desquamation/scaling (D)—is assessed on a 5-point scale: 0 (none), 1 (mild), 2 (moderate), 3 (severe) or 4 (very severe).

Orticumab is a human monoclonal antibody that contains heavy chain complementarity determining regions (HCDR) 1 (HCDR1), 2 (HCDR2) and 3 (HCDR3) as set forth in SEQ ID Nos: 2, 3 and 4, respectively; and light chain complementarity determining regions (LCDR) 1 (LCDR1), 2 (LCDR2) and 3 (LCDR3) as set forth in SEQ ID Nos: 5, 6 and 7, respectively. Orticumab contains a variable heavy region ($V_H$) amino acid sequence of SEQ ID No: 8, a variable light region ($V_L$) amino acid sequence of SEQ ID No: 9. Orticumab contains a heavy chain amino acid sequence of SEQ ID No: 10, a light chain amino acid sequence of SEQ ID No: 11.

HCDR1, i.e., SEQ ID No.: 2, is: FSNAWMSWVRQAPG.
HCDR2, i.e., SEQ ID No.: 3, is: SSISVGGHRTYY-ADSVKGR.
HCDR3, i.e., SEQ ID No.: 4, is: ARIRVGPSGGAFDY.
LCDR1, i.e., SEQ ID No.: 5, is: CSGSNTNIGKNYVS.
LCDR2, i.e., SEQ ID No.: 6, is: ANSNRPS.
LCDR3, i.e., SEQ ID No.: 7, is: CASWDASLNGWV.

Variable heavy region ($V_H$), i.e., SEQ ID No.:8, is as shown:

```
EVQLLESGGG LVQPGGSLRL SCAASGFTFS NAWMSWVRQA

PGKGLEWVSS ISVGGHRTYY ADSVKGRSTI SRDNSKNTLY

LQMNSLRAED TAVYYCARIR VGPSGGAFDY WGQGTLVTVS.
```

Variable light region ($V_L$), i.e., SEQ ID No.: 9, is as shown:

```
QSVLTQPPSA SGTPGQRVTI SCSGSNTNIG KNYVSWYQQL

PGTAPKLLIY ANSNRPSGVP DRFSGSKSGT SASLAISGLR

SEDEADYYCA SWDASLNGWV FGGGTKLTVL.
```

Heavy chain, i.e., SEQ ID No.:10, is as shown:

```
EVQLLESGGG LVQPGGSLRL SCAASGFTFS NAWMSWVRQA

PGKGLEWVSS ISVGGHRTYY ADSVKGRSTI SRDNSKNTLY

LQMNSLRAED TAVYYCARIR VGPSGGAFDY WGQGTLVTVS

SASTKGPSVF PLAPSSKSTS GGTAALGCLV KDYFPEPVTV

SWNSGALTSG VHTFPAVLQS SGLYSLSSVV TVPSSSLGTQ

TYICNVNHKP SNTKVDKKVE PKSCDKTHTC PPCPAPELLG

GPSVFLFPPK PKDTLMISRT PEVTCVVVDV SHEDPEVKFN

WYVDGVEVHN AKTKPREEQY NSTYRVVSVL TVLHQDWLNG

KEYKCKVSNK ALPAPIEKTI SKAKGQPREP QVYTLPPSRD

ELTKNQVSLT CLVKGFYPSD IAVEWESNGQ PENNYKTTPP

VLDSDGSFFL YSKLTVDKSR WQQGNVFSCS VMHEALHNHY

TQKSLSLSPG K.
```

Light chain, i.e., SEQ ID No.:11, is as shown:

```
QSVLTQPPSA SGTPGQRVTI SCSGSNTNIG KNYVSWYQQL

PGTAPKLLIY ANSNRPSGVP DRFSGSKSGT SASLAISGLR

SEDEADYYCA SWDASLNGWV FGGGTKLTVL GQPKAAPSVT

LFPPSSEELQ ANKATLVCLI SDFYPGAVTV AWKADSSPVK

AGVETTTPSK QSNNKYAASS YLSLTPEQWK SHRSYSCQVT

HEGSTVEKTV APTECS.
```

Methods are provided of treating or reducing the severity of psoriasis in a subject including administering to the subject an effective amount of an antibody or antibody fragment that binds a fragment set forth in SEQ ID No.: 1 of apoB100, and the antibody contains one or more of HCDR1, HCDR2, HCDR3, LCDR1, LCDR2 and LCDR3 as set forth in SEQ ID Nos.: 2-7, respectively.

Methods of treating or reducing the severity of psoriasis in a subject are also provided including administering to the subject an effective amount of an antibody or antibody fragment that binds a fragment set forth in SEQ ID No.: 1 of apoB100, and the antibody contains one or more of HCDR1, HCDR2, HCDR3, LCDR1, LCDR2 and LCDR3 as set forth in SEQ ID Nos.: 2-7, respectively.

The antibody containing "one or more of HCDR1, HCDR2, HCDR3, LCDR1, LCDR2 and LCDR3" encompasses embodiments that the antibody contains one, any two, any three, any four, any five or all six of the CDRs (i.e., HCDR1, HCDR2, HCDR3, LCDR1, LCDR2 and LCDR3).

One aspect of the invention provides an antibody comprising at least one complementarity determining region (CDR) that has the amino acid sequence of the corresponding CDR of antibody orticumab; that more preferably, the antibody has two or three or four or five CDRs that have the sequence of the corresponding CDRs of antibody orticumab; that if the antibody has three or four CDRs that have the sequence of the corresponding CDRs of antibody orticumab, it is preferred if the antibody has all three heavy chain or all three light chain CDRs that have the sequence of the corresponding CDRs of antibody orticumab; that thus this aspect of the invention includes an antibody comprising three light chain CDRs that have the sequence of the corresponding three light chain CDRs of antibody orticumab, or three heavy chain CDRs that have the sequence of the corresponding three heavy chain CDRs of antibody orticumab; that yet more preferably, the antibody comprises three light chain CDRs and three heavy chain CDRs that have the sequence of the corresponding CDRs of antibody orticumab; that if the antibody does not comprise all six CDRs that have the sequence of the corresponding CDRs of antibody orticumab, it is preferred if some or all of the 1, 2, 3, 4 or 5 "non-identical" CDRs comprise a variant of the sequence of the corresponding CDRs of antibody orticumab, (by "a variant" we includes the meaning that the variant has at least 50% sequence identity with the sequence of the corresponding CDR, more preferably at least 70%, yet more preferably at least 80% or at least 90% or at least 95%; most preferably, the variant has 96% or 97% or 98% or 99% sequence identity with the sequence of the corresponding CDR of antibody orticumab; typically the "variant" CDR sequence has 5 or 4 or 3 or 2 or only 1 amino acid residue difference from the sequence of the corresponding CDR of antibody orticumab); and that this aspect of the invention includes antibody orticumab. For example, one aspect of the embodiment provides that the administered antibody contains HCDR1 as set forth in SEQ ID No.: 2. Another aspect provides that the administered antibody contains HCDR2 as set forth in SEQ ID No.: 3. Another aspect provides that the administered antibody contains HCDR3 as set forth in SEQ ID No.: 4. Yet another aspect provides that the administered antibody contains LCDR1 as set forth in SEQ ID No.: 5. Another aspect provides that the administered antibody contains LCDR2 as set forth in SEQ ID No.: 6. Another aspect provides that the administered antibody contains LCDR3 as set forth in SEQ ID No.:7. Yet another aspect provides that the administered antibody contains HCDR1 as set forth in SEQ ID No.:2 and HCDR2 as set forth in SEQ ID No.: 3. Another aspect provides that the administered antibody contains HCDR1 as set forth in SEQ ID No.:2 and HCDR3 as set forth in SEQ ID No.: 4. Another aspect provides that the administered antibody contains HCDR1 as set forth in SEQ ID No.:2 and LCDR1 as set forth in SEQ ID No.: 5. Another aspect provides that the administered antibody contains HCDR1 as set forth in SEQ ID No.:2 and LCDR2 as set forth in SEQ ID No.: 6. Another aspect provides that the administered antibody contains HCDR1 as set forth in SEQ ID No.:2 and LCDR3 as set forth in SEQ ID No.: 7. Another aspect provides that the administered antibody contains HCDR2 as set forth in SEQ ID No.:3 and HCDR3 as set forth in SEQ ID No.: 4. Another aspect provides that the administered antibody contains HCDR2 as set forth in SEQ ID No.:3 and LCDR1 as set forth in SEQ ID No.: 5. Another aspect provides that the administered antibody contains HCDR2 as set forth in SEQ ID No.:3 and LCDR2 as set forth in SEQ ID No.: 6. Another aspect provides that the administered antibody contains HCDR2 as set forth in SEQ ID No.:3 and LCDR3 as set forth in SEQ ID No.: 7. Another aspect provides that the administered antibody contains HCDR3 as set forth in SEQ ID No.:4 and LCDR1 as set forth in SEQ ID No.: 5. Another aspect provides that the administered antibody contains HCDR3 as set forth in SEQ ID No.:4 and LCDR2 as set forth in SEQ ID No.: 6. Another aspect provides that the administered antibody contains HCDR3 as set forth in SEQ ID No.:4 and LCDR3 as set forth in SEQ ID No.: 7. Another aspect provides that the administered antibody contains LCDR1 as set forth in SEQ ID No.:5 and LCDR2 as set forth in SEQ ID No.: 6. Another aspect provides that the administered antibody contains LCDR1 as set forth in SEQ ID No.:5 and LCDR3 as set forth in SEQ ID No.: 7. Another aspect provides that the administered antibody contains LCDR2 as set forth in SEQ ID No.:6 and LCDR3 as set forth in SEQ ID No.: 7. Another aspect provides that the administered antibody contains HCDR1, HCDR2 and HCDR3 as set forth in SEQ ID Nos.: 2-4, respectively. Another aspect provides that the administered antibody contains HCDR1, HCDR2 and LCDR1 as set forth in SEQ ID Nos.: 2, 3 and 5, respectively. Another aspect provides that the administered antibody contains HCDR1, HCDR2 and LCDR2 as set forth in SEQ ID Nos.: 2, 3 and 6, respectively. Another aspect provides that the administered antibody contains HCDR1, HCDR2 and LCDR3 as set forth in SEQ ID Nos.: 2, 3 and 7, respectively. Another aspect provides that the administered antibody contains HCDR1, HCDR3 and LCDR1 as set forth in SEQ ID Nos.: 2, 4 and 5, respectively. Another aspect provides that the administered antibody contains HCDR1, HCDR3 and LCDR2 as set forth in SEQ ID Nos.: 2, 4 and 6, respectively. Another aspect provides that the administered antibody contains HCDR1, HCDR3 and LCDR3 as set forth in SEQ ID Nos.: 2, 4 and 7, respectively. Another aspect provides that the administered antibody contains HCDR1, LCDR1 and LCDR2 as set forth in SEQ ID Nos.: 2, 5 and 6, respectively. Another aspect provides that the administered antibody contains HCDR1, LCDR1 and LCDR3 as set forth in SEQ ID Nos.: 2, 5 and 7, respectively. Another aspect provides that the administered antibody contains HCDR1, LCDR2 and LCDR3 as set forth in SEQ ID Nos.: 2, 6 and 7, respectively. Another aspect provides that the administered antibody contains HCDR2, HCDR3 and LCDR1 as set forth in SEQ ID Nos.: 3, 4 and 5, respectively. Another aspect provides that the administered antibody contains HCDR2, HCDR3 and LCDR2 as set forth in SEQ ID Nos.: 3, 4 and 6, respectively. Another aspect provides that the administered antibody contains HCDR2, HCDR3 and LCDR3 as set forth in SEQ ID Nos.: 3, 4 and 7, respectively. Another aspect provides that the administered antibody contains HCDR2, LCDR1 and LCDR2 as set forth in SEQ ID Nos.: 3, 5 and 6, respectively. Another aspect provides that the administered antibody contains HCDR2, LCDR1 and LCDR3 as set forth in SEQ ID Nos.: 3, 5 and 7, respectively. Another aspect provides that the administered antibody contains HCDR2, LCDR2 and LCDR3 as set forth in SEQ ID Nos.: 3, 6 and 7, respectively. Another aspect provides that the administered antibody contains HCDR3, LCDR1 and LCDR2 as set forth in SEQ ID Nos.:4, 5 and 6, respectively. Another aspect provides that the administered antibody contains HCDR3, LCDR1 and LCDR3 as set forth in SEQ ID Nos.:4, 5 and 7, respectively. Another aspect provides that the administered antibody contains HCDR3, LCDR2 and LCDR3 as set forth in SEQ ID Nos.:4, 6 and 7, respectively. Another aspect provides that the administered antibody contains LCDR1, LCDR2 and LCDR3 as set forth in SEQ ID Nos.:5-7, respectively. Yet another aspect provides that the administered antibody contains HCDR1, HCDR2, HCDR3 and LCDR1 as set forth in SEQ ID Nos.:2-5, respectively. Another aspect provides that the administered antibody contains HCDR1, HCDR2, HCDR3 and LCDR2 as set forth in SEQ ID Nos.:2-4 and 6, respectively. Another aspect provides that the administered antibody contains HCDR1, HCDR2, HCDR3 and LCDR3 as set forth in SEQ ID Nos.:2-4 and 7, respectively. Another aspect provides that the administered antibody contains HCDR1, HCDR2, LCDR1 and LCDR2 as set forth in SEQ ID Nos.:2, 3, 5 and 6, respectively. Another aspect provides that the administered antibody contains HCDR1, HCDR2, LCDR1 and LCDR3 as set forth in SEQ ID Nos.:2, 3, 5 and 7, respectively. Another aspect provides that the administered antibody contains HCDR1, HCDR2, LCDR2 and LCDR3 as set forth in SEQ ID Nos.:2, 3, 6 and 7, respectively. Another aspect provides that the administered antibody contains HCDR1, HCDR3, LCDR1 and LCDR2 as set forth in SEQ ID Nos.:2, 4, 5 and 6, respectively. Another aspect provides that the administered antibody contains HCDR1, HCDR3, LCDR1 and LCDR3 as set forth in SEQ ID Nos.:2, 4, 5 and 7, respectively. Another aspect provides that the administered antibody contains HCDR1, HCDR3, LCDR2 and LCDR3 as set forth in SEQ ID Nos.:2, 4, 6 and 7, respectively. Another aspect provides that the administered antibody contains HCDR1, LCDR1, LCDR2 and LCDR3 as set forth in SEQ ID Nos.:2, 5, 6 and 7, respectively. Another aspect provides that the administered antibody contains HCDR2, HCDR3, LCDR1 and LCDR2 as set forth in SEQ ID Nos.:3-6, respectively. Another aspect provides that the administered antibody contains HCDR2, HCDR3, LCDR1 and LCDR3 as set forth in SEQ ID Nos.:3-5 and 7, respectively. Another aspect provides that the administered antibody contains HCDR2, HCDR3, LCDR2 and LCDR3 as set forth in SEQ ID Nos.:3, 4, 6 and 7, respectively. Another aspect provides that the administered antibody contains HCDR2, LCDR1, LCDR2 and LCDR3 as set forth in SEQ ID Nos.:3, 5, 6 and 7, respectively. Another aspect provides that the administered antibody contains HCDR3, LCDR1, LCDR2 and LCDR3 as set forth in SEQ ID Nos.:4, 5, 6 and 7, respectively. Yet another aspect provides that the administered antibody contains HCDR1, HCDR2, HCDR3, LCDR1 and LCDR2 as set forth in SEQ ID Nos.: 2-6 respectively. Another aspect provides that the administered antibody contains HCDR1, HCDR2, HCDR3, LCDR1 and LCDR3 as set forth in SEQ ID Nos.: 2-5 and 7 respectively. Another aspect provides that the administered antibody contains HCDR1, HCDR2, HCDR3, LCDR2 and LCDR3 as set forth in SEQ ID Nos.: 2, 3, 4, 6 and 7 respectively. Another aspect provides that the administered antibody contains HCDR1, HCDR2, LCDR1, LCDR2 and LCDR3 as set forth in SEQ ID Nos.: 2, 3, 5-7, respectively. Another aspect provides that the administered antibody contains HCDR1, HCDR3, LCDR1, LCDR2 and LCDR3 as set forth in SEQ ID Nos.: 2, 4-7, respectively. Another aspect provides that the administered antibody contains HCDR2, HCDR3, LCDR1, LCDR2 and LCDR3 as set forth in SEQ ID Nos.: 3-7, respectively. Yet another aspect provides that the administered antibody contains HCDR1, HCDR2, HCDR3, LCDR1, LCDR2 and LCDR3 as set forth in SEQ ID Nos.: 2-7, respectively.

A further aspect of the invention provides that the method of treating, reducing the severity of psoriasis, or providing passive immunity to a subject against psoriasis, consists of administering to the subject an effective amount of an antibody or antibody fragment that binds a fragment set forth in SEQ ID No.: 1 of apoB100, and the antibody contains HCDR1, HCDR2, HCDR3, LCDR1, LCDR2 and LCDR3 as set forth in SEQ ID Nos.: 2-7, respectively.

Methods are provided of treating or reducing the severity of psoriasis including administering to the subject an effective amount of an antibody or antibody fragment that binds a fragment set forth in SEQ ID No.: 1 of apoB100, and the antibody contains a variable heavy region ($V_H$) as set forth in SEQ ID No.: 8 and a variable light region ($V_L$) containing LCDR1, LCDR2 and LCDR3 as set forth in SEQ ID Nos.: 5-7, respectively. A further aspect provides that the method of treating or reducing the severity of psoriasis, and/or provide passive immunity, includes administering to the subject an effective amount of an antibody or antibody fragment that binds a fragment set forth in SEQ ID No.: 1 of apoB100, and the antibody contains a variable light region ($V_L$) of SEQ ID No.: 9 and a variable heavy region ($V_H$) that contains HCDR1, HCDR2 and HCDR3 as set forth in SEQ ID Nos.: 2-4, respectively. Yet another aspect of the invention provides that the method of treating, reducing the severity of psoriasis, and/or reducing the likelihood of psoriasis in a subject, includes administering to the subject an effective amount of an antibody or antibody fragment that binds a fragment set forth in SEQ ID No.: 1 of apoB100, and the antibody contains a variable heavy region ($V_H$) of SEQ ID No.: 8 and a variable light region ($V_L$) of SEQ ID No.: 9.

Methods are provided of reducing the likelihood of psoriasis, or providing passive immunity to a subject against psoriasis, including administering to the subject an effective amount of an antibody or antibody fragment that binds a fragment set forth in SEQ ID No.: 1 of apoB100, and the antibody contains a variable heavy region ($V_H$) as set forth in SEQ ID No.: 8 and a variable light region ($V_L$) containing LCDR1, LCDR2 and LCDR3 as set forth in SEQ ID Nos.: 5-7, respectively. A further aspect provides that the method of treating, reducing the severity of psoriasis, and/or reducing the likelihood of psoriasis, in a subject includes administering to the subject an effective amount of an antibody or antibody fragment that binds a fragment set forth in SEQ ID No.: 1 of apoB100, and the antibody contains a variable light region ($V_L$) of SEQ ID No.: 9 and a variable heavy region ($V_H$) that contains HCDR1, HCDR2 and HCDR3 as set forth in SEQ ID Nos.: 2-4, respectively. Yet another aspect of the invention provides that the method of treating, reducing the severity of psoriasis, and/or reducing the likelihood of having psoriasis in a subject, includes administering to the subject an effective amount of an antibody or antibody fragment that binds a fragment set forth in SEQ ID No.: 1 of apoB100, and the antibody contains a variable heavy region ($V_H$) of SEQ ID No.: 8 and a variable light region ($V_L$) of SEQ ID No.: 9.

Methods are also provided of treating or reducing the severity of psoriasis, which includes administering to the subject an effective amount of an antibody or antibody fragment that binds a fragment set forth in SEQ ID No.: 1 of apoB100, and the antibody contains a heavy chain of SEQ ID No.: 10 and a light chain containing LCDR1, LCDR2 and LCDR3 as set forth in SEQ ID Nos.: 5-7, respectively. A further aspect of the embodiment provides that the method includes administering to the subject an effective amount of an antibody or antibody fragment that binds a fragment set forth in SEQ ID No.: 1 of apoB100, and the antibody contains a heavy chain of SEQ ID No.: 10 and a light chain that contains a variable light region ($V_L$) of SEQ ID No.: 9. Another aspect of the invention provides the method includes administering to the subject an effective amount of an antibody or antibody fragment that binds a fragment set forth in SEQ ID No.: 1 of apoB100, and the antibody contains a light chain of SEQ ID No.: 11 and a heavy chain that contains HCDR1, HCDR2 and HCDR3 as set forth in SEQ ID Nos.: 2-4, respectively. Yet another aspect provides the method includes administering to the subject an effective amount of an antibody or antibody fragment that binds a fragment set forth in SEQ ID No.: 1 of apoB100, and the antibody contains a light chain of SEQ ID No.: 11 and a heavy chain that contains a variable heavy region ($V_H$) of SEQ ID No.: 8. Alternatively, the method includes administering to the subject an effective amount of an antibody or antibody fragment that binds a fragment set forth in SEQ ID No.: 1 of apoB100, and the antibody contains a heavy chain of SEQ ID No.: 10 and a light chain of SEQ ID No.: 11.

Methods are also provided of reducing the likelihood of psoriasis, or providing passive immunity to a subject against psoriasis, which includes administering to the subject an effective amount of an antibody or antibody fragment that binds a fragment set forth in SEQ ID No.: 1 of apoB100, and the antibody contains a heavy chain of SEQ ID No.: 10 and a light chain containing LCDR1, LCDR2 and LCDR3 as set forth in SEQ ID Nos.: 5-7, respectively. A further aspect of the embodiment provides that the method includes administering to the subject an effective amount of an antibody or antibody fragment that binds a fragment set forth in SEQ ID No.: 1 of apoB100, and the antibody contains a heavy chain of SEQ ID No.: 10 and a light chain that contains a variable light region ($V_L$) of SEQ ID No.: 9. Another aspect of the invention provides the method includes administering to the subject an effective amount of an antibody or antibody fragment that binds a fragment set forth in SEQ ID No.: 1 of apoB100, and the antibody contains a light chain of SEQ ID No.: 11 and a heavy chain that contains HCDR1, HCDR2 and HCDR3 as set forth in SEQ ID Nos.: 2-4, respectively. Yet another aspect provides the method includes administering to the subject an effective amount of an antibody or antibody fragment that binds a fragment set forth in SEQ ID No.: 1 of apoB100, and the antibody contains a light chain of SEQ ID No.: 11 and a heavy chain that contains a variable heavy region ($V_H$) of SEQ ID No.: 8. Alternatively, the method includes administering to the subject an effective amount of an antibody or antibody fragment that binds a fragment set forth in SEQ ID No.: 1 of apoB100, and the antibody contains a heavy chain of SEQ ID No.: 10 and a light chain of SEQ ID No.:

Further embodiments of the methods include administering an inhibitor of native LDL, oxidized LDL (oxLDL) or MDA-modified LDL, which are suitable for treatment of a subject diagnosed with psoriasis and reducing the severity of psoriasis, and optionally also reducing the severity or the likelihood of developing atherosclerosis, in the subject. In one embodiment, the inhibitor is an anti-oxLDL antibody or an antigen-binding fragment thereof capable of binding an oxidized fragment of apolipoprotein B100. In another embodiment, the inhibitor of oxidized LDL is a small molecule, a polypeptide, a peptide, or a nucleic acid molecule, which is capable of binding an oxidized fragment of apolipoprotein B100. In other embodiments, the inhibitor of oxidized LDL is an antibody or an antigen-binding fragment capable of binding a malondialdehyde-modified LDL. In exemplary embodiments, the inhibitor of oxidized or malondialdehyde-modified LDL is a monoclonal antibody, such as orticumab, targeting an oxidized or MDA-modified form of a LDL.

Patient Selection

The methods disclosed herein, in some embodiments, include treating or inhibiting one or more forms of psoriasis with administering an effective amount of orticumab to a subject in need thereof.

Some embodiments provided in the disclosed methods further include selecting a subject showing symptoms of psoriasis or having been diagnosed with psoriasis. For example, subjects with psoriasis can be characterized by an elevated amount of tumor necrosis factor-alpha (TNFα), interleukin 6 (IL-6), C-reactive protein (CRP), or a combination thereof, compared to a control subject free of psoriasis. In some aspects, the methods are for treatment in subjects that are refractory to typical therapies to psoriasis (e.g., UVA or UVB therapy; topical steroids).

In other embodiments, methods of treating or inhibiting the development of plaque psoriasis are provided with administering an effective amount of orticumab to a subject with plaque psoriasis, and the subject does not have non-plaque forms of psoriasis such as erythrodermic, guttate or pustular at least at the time of the administration.

Various embodiments provide the psoriasis in the disclosed methods herein is plaque psoriasis and does not include a non-plaque form of psoriasis, such as erythrodermic, guttate or pustular psoriasis.

Other embodiments of the methods of treating or reducing the severity of psoriasis include selecting a subject exhibiting symptoms of or having been diagnosed with plaque psoriasis, and administering to the subject an antibody or antibody fragment thereof according to any of the aforementioned antibody features.

A further aspect of the invention provides the methods of treating, reducing the severity of psoriasis, and/or reducing the likelihood of psoriasis, include administering to the subject an antibody or antibody fragment thereof according to any of the aforementioned antibody features, wherein the subject exhibits symptoms of plaque psoriasis or has been diagnosed with plaque psoriasis, but does not show symptoms of erythrodermic, guttate or pustular psoriasis.

Yet other embodiments provide the subject in the methods disclosed herein has further been diagnosed with, or shows symptoms of, atherosclerosis, and the methods further reduce symptoms of atherosclerosis besides plaque psoriasis. For example, a method of treating or reducing the severity of psoriasis and atherosclerosis includes administering to the subject an effective amount of an antibody or antibody fragment that binds an epitope set forth in SEQ ID No.:1, and the antibody is orticumab or antigen-binding fragment thereof, and wherein the subject exhibits symptoms of plaque psoriasis and atherosclerosis.

Also provided with the methods are embodiments where the subject does not have, has not been diagnosed with, or does not show symptoms of atherosclerosis.

Other embodiments of the invention provide a method of treating or inhibiting the development of psoriatic arthritis by administering an effective amount of orticumab to a subject in need thereof. The subject in some embodiments is diagnosed with, shows symptoms of, or has psoriatic arthritis In some embodiments, the methods described above for treating, reducing the severity of, slowing progression of or inhibiting a combination of psoriasis and atherosclerosis in a subject in need thereof is characterized by reduced amounts of plaque psoriasis following administration of an anti-oxLDL antibody that binds to SEQ ID No.:1 of ApoB100, compared to those levels of the subject before administration of the anti-oxLDL antibody.

Combination Therapy

Further embodiments provide that the methods of treating or reducing the severity of psoriasis include administering an effective amount of an antibody or antibody fragment in combination with another therapeutic agent to the subject. Embodiments are also provided of the methods of reducing the likelihood of psoriasis in a subject, which includes administering an effective amount of an antibody or antibody fragment in combination with another therapeutic agent to the subject. Exemplary therapeutic agents for use in this combination include corticosteroids (e.g., cortisol, corticosterone, cortisone, aldosterone), vitamin D analogues (e.g., calcipotriol, maxacalcitol, tacalcitol and calcitriol), retinoids (e.g., soriatane, acitretin, and tazarotene), keratolytic agents (e.g., salicylic acid), coal tar, ultraviolet (UV) A therapy, UV B therapy, inhibitors of TNFα (e.g., anti-TNFα antibodies such as infliximab, adalimumab, certolizumab pegol, golimumab, etanercept; thalidomide, lenalidomide, pomalidomide; xanthine derivatives such as pentoxifylline; bupropion), anti-IL-12/23 antibodies (e.g., ustekinumab, STELARA®), anti-IL-23 antibodies that bind IL-23 alone but not IL-12 (e.g., risankizumab, guselkumab, tildrakizumab), and anti-IL-17 antibodies (e.g., secukinumab, ixekizumab, brodalumab).

The methods may also include administering an antibody or antibody fragment that binds SEQ ID No.:1, another therapeutic agent, and commonly used adjuvants to enhance absorption of the antibody or mixture of antibodies.

In various embodiments, the composition to be administered in the disclosed methods are formulated for delivery via any route of administration. For example, the methods include administration via an aerosol, nasal, oral, transmucosal, transdermal, parenteral or enteral route. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection.

Dosage

Typically, an effective amount of the anti-oxLDL or an anti-LDL antibody, or the antibody that binds SEQ ID No.:1, in the method disclosed herein, results in a plasma concentration of at least 4 µg/mL, preferably at least 12 µg/mL in the subject.

Embodiments provide the method of treating or reducing the severity of psoriasis in a subject includes administering to the subject an antibody or antibody fragment disclosed above subcutaneously at about 330 mg/month for about 3, 4, 5, 6, 7, 8, 9, 10, 11 or 12 months or longer, and the subject is an adult human.

Other embodiments provide administering the antibody or antibody fragment to treat psoriasis or provide passive immunity at at least 8 mg orticumab/kg of a patient (e.g., 664 mg for an averaged human patient of 83 kg). Some embodiments provide administering the antibody or antibody fragment at between 5 mg orticumab/kg of a patient (e.g., 415 mg for an averaged human patient of 83 kg) and 8 mg/kg. Some embodiment provides administering orticumab at a monthly dosing regimen at the above-mentioned dosage.

Other embodiments provide administering the antibody or antibody fragment to treat psoriasis weekly at no less than 2 mg/kg/week (166 mg for an averaged human patient of 83 kg); preferably, 4 mg/kg/week (332 mg for an averaged human patient of 83 kg). In another aspect, the composition of an anti-oxLDL antibody is administered biweekly at ≥2.5 mg/kg/two weeks (e.g., 208 mg for an averaged human patient of 83 kg). In yet another aspect, the composition of an anti-oxLDL antibody is administered monthly at about 6 mg/kg/month (e.g., about 498 mg for an averaged human patient of 83 kg). For example, the monthly dosing may be carried out for 12 months or 3 months.

Yet other embodiments provide administering an antibody or antibody fragment to treat psoriasis with at least an initial dose of 800-900 mg, 900-1000 mg, 1000-1100 mg, 1100-1200 mg, 1200-1300 mg, 1300-1400 mg, 1400-1500 mg, or 1500-1600 mg. In some aspects, the effective amount in the method described herein includes an initial dose of orticumab of approximately 1000-1500 mg, followed by subsequent doses of the antibody at 700-900 mg administered weekly for 2, 3, 4 or 5 weeks and/or even administered monthly for 1, 2 or 3 months.

Other embodiments provide administering step-wise escalating doses of an antibody against native or oxidized LDL (e.g., binding SEQ ID No.:1). In this embodiment, an exemplary (starting) dose of a single-dose administration of an antibody (e.g., orticumab) against native or oxidized LDL is between 0.005 and 0.01 mg/kg (e.g., intravenously); and other exemplary dosage levels to be administered in the single-dose administration are between 0.01 and 0.15, between 0.15 and 0.75, between 0.75 and 2.5, between 2.5 and 7.5, and between 7.5 and 30 mg/kg (e.g., intravenously). For example, a starting dose of orticumab in a single-dose intravenous administration is 0.007 mg/kg; and other exemplary dosages can be 0.05, 0.25, 1.25, 5.0 or 15.0 mg/kg in subsequent single-dose intravenous administration. In another embodiment, a single-dose subcutaneous administration of an antibody against native or oxidized LDL is between 0.5 and 5 mg/kg, and a multiple-dose subcutaneous administration is also between 0.5 and 5 mg/kg. For example, an antibody against native or oxidized LDL at 1.25 mg/kg is administered subcutaneously. In various embodiments, the dosage is administered within a specified hour range of the day in each administration, and each dose in a multiple-dose treatment (e.g., 4 doses, 3 doses, 5 doses, or 6 doses) is administered at weekly intervals with a time window of ±1 day. In another example, an antibody (such as orticumab) against native or oxidized LDL is administered at between 300 mg and 450 mg (e.g., 360 mg) to a human subject, optionally followed by another dose between 300 mg and 450 mg (e.g., 360 mg) to the human subject where the second dose is at least 70 days (up to 91 days) apart from the first dose. The antibody (such as orticumab) may be formulated at a concentration of 100-170 mg/mL (e.g., 150 mg/mL) and for use in subcutaneous administration without further dilution, or diluted to a large volume for intravenous infusion.

Further embodiments include administering to a subject an effective amount of an antibody or antibody fragment that binds SEQ ID No.:1 and having a sequence of one or more of SEQ ID Nos: 2-11, which is in the range of about 10-50 µg/period, 50-100 µg/period, 100-150 µg/period, 150-200 µg/period, 100-200 µg/period, 200-300 µg/period, 300-400 µg/period, 400-500 µg/period, 500-600 µg/period, 600-700 µg/period, 700-800 µg/period, 800-900 µg/period, 900-1000 µg/period, 1000-1100 µg/period, 1100-1200 µg/period, 1200-1300 µg/period, 1300-1400 µg/period, 1400-1500 µg/period, 1500-1600 µg/period, 1600-1700 µg/period, 1700-1800 µg/period, 1800-1900 µg/period, 1900-2000 µg/period, 2000-2100 µg/period, 2100-2200 µg/period, 2200-2300 µg/period, 2300-2400 µg/period, 2400-2500 µg/period, 2500-2600 µg/period, 2600-2700 µg/period, 2700-2800 µg/period, 2800-2900 µg/period or 2900-3000 µg/period. A period is a day, a week, a month, or another length of time. One aspect is the antibody (e.g., orticumab) is administered at a weekly, biweekly or monthly frequency of any of above-mentioned dosage per period.

In some embodiments, the methods include administering an inhibitor of oxidized LDL (e.g., orticumab) to the subject for 1-5 days, 1-5 weeks, 1-5 months, or 1-5 years. For example, the antibody is administered to the subject in 3, 4, 5, 6, 7, 8, 9, 10, 11, 12, 13, 14, 15, 16, 17, 18, 19 or 20 doses, each dose separated by at least 3 days, 5 days, one week, two weeks, one month, two months, or a combination thereof. In other embodiments, the second dose is administered about 2-3 weeks, or about 3 weeks after the first dose and the third dose is administered about 5-6 weeks or about 6 weeks after the first dose, etc. In another embodiment, the second dose is administered about 2-3 months, about 2 months, about 3 months or about 4 months after the first dose and the third dose is administered about 4-6 months, about 5-6 months, about 5 months or about 6 months after the first dose.

Other embodiments provide administering step-wise escalating doses of an antibody against native or oxidized LDL to treat psoriasis or provide passive immunity. In this embodiment, an exemplary (starting) dose of a single-dose administration of an antibody (e.g., orticumab) against native or oxidized LDL is between 0.005 and 0.01 mg/kg (e.g., intravenously); and other exemplary dosage levels to be administered in the single-dose administration are between 0.01 and 0.15, between 0.15 and 0.75, between 0.75 and 2.5, between 2.5 and 7.5, and between 7.5 and 30 mg/kg (e.g., intravenously). For example, a starting dose of orticumab in a single-dose intravenous administration is 0.007 mg/kg; and other exemplary dosages can be 0.05, 0.25, 1.25, 5.0 or 15.0 mg/kg in subsequent single-dose intravenous administration. In another embodiment, a single-dose subcutaneous administration of an antibody against native or oxidized LDL is between 0.5 and 5 mg/kg, and a multiple-dose subcutaneous administration is also between 0.5 and 5 mg/kg. For example, an antibody against native or oxidized LDL at 1.25 mg/kg is administered subcutaneously. In various embodiments, the dosage is administered within a specified hour range of the day in each administration, and each dose in a multiple-dose treatment (e.g., 4 doses, 3 doses, 5 doses, or 6 doses) is administered at weekly intervals with a time window of ±1 day. In another example, an antibody (such as orticumab) against native or oxidized LDL is administered at between 300 mg and 450 mg (e.g., 360 mg) to a human subject, optionally followed by another dose between 300 mg and 450 mg (e.g., 360 mg) to the human subject where the second dose is at least 70 days (up to 91 days) apart from the first dose. The antibody (such as orticumab) may be formulated at a concentration of 100-170 mg/mL (e.g., 150 mg/mL) and for use in subcutaneous administration without further dilution, or diluted to a large volume for intravenous infusion. In some embodiments, the therapeutically effective amount of an anti-LDL antibody or an anti-oxLDL antibody, or analogs, pharmaceutical equivalents or a peptidomimetics thereof, for use with the methods described herein is per dose: 1-10 µg/kg, 10-100 µg/kg, 100-500 µg/kg, 200-500 µg/kg, 300-500 µg/kg, 400-500 µg/kg, 1-5 mg/kg, 5-10 mg/kg, 10-15 mg/kg, 15-20 mg/kg, 20-25 mg/kg, 25-50 mg/kg, 50-75 mg/kg of the subject; where each dose is administered daily, weekly, monthly, or at other intervals.

In some embodiments, an instruction manual for use, a vial for diluent, or both are also included in the kit, in addition to the one or the plurality of vials/doses of the antibody or antibody fragment to treat psoriasis.

Compositions or Medicaments

In various embodiments, the present invention provides a pharmaceutical composition for use in the methods of treating, reducing the severity of psoriasis and/or reducing the likelihood of psoriasis described herein. The pharmaceutical composition includes an inhibitor of oxidized LDL, such as an anti-oxLDL antibody that binds to an epitope of SEQ ID No.:1 of ApoB100, and a pharmaceutically acceptable carrier. Further embodiments provide that a composition or medicament for use in treating, reducing the severity of, or promoting prophylaxis against psoriasis, or treating, reducing the severity of, or promoting prophylaxis against atherosclerosis in a subject exhibiting symptoms of or having been diagnosed with psoriasis, where the composition of medicament contains an anti-oxLDL antibody that binds to an epitope of SEQ ID No.:1 of ApoB100, as disclosed above, in an amount of between 300 mg and 400 mg, preferably about 330 mg, per dosage (or vial), optionally with a pharmaceutically acceptable carrier, each (e.g., for a monthly subcutaneous administration to a subject) for 1, 2, 3, 4, 5, 6, 7, 8, 9, 10, 11, 12 months or longer. Other embodiments provide the composition or medicament contains an anti-oxLDL antibody that binds to an epitope of SEQ ID No.:1 of ApoB100, as disclosed above, in an amount of at least 5, 6, 7, or 8 mg orticumab/kg of a patient in one dosage (or vial), and optionally more dosages (or vials) of at least 2 mg/kg/week, at least 2.5 mg/kg/two weeks, or at least 6 mg/kg/month, for 3, 4, 5, 6, 7, 8, 9, 10, 11, 12 months or longer. Further embodiments provide the composition or medicament contains the antibody (such as orticumab) at a concentration of 100-170 mg/mL (e.g., 150 mg/mL) and for use in subcutaneous administration without further dilution, or diluted to a large volume for intravenous infusion.

"Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof. Generally, each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Prepare Antibodies in the Methods

In some embodiments, the aforementioned methods involve antibodies that bind to a specific antigen epitope, where the antibodies contain one or more defined sequences. For example, modern recombinant library technology is used to prepare therapeutic antibodies against native ApoB, oxidized ApoB or MDA-modified ApoB. While murine hybridomas cells produce large amounts of identical antibodies, these non-human antibodies are recognized by human body as foreign, and as a consequence, their efficacy and plasma half-lives are decreased in addition to eliciting allergic reactions. To solve this problem, one approach is to make chimeric antibodies where the murine variable domains of the antibody are transferred to human constant regions resulting in an antibody that is mainly human. A further refinement of this approach is to develop humanized antibodies where the regions of the murine antibody that contacted the antigen, the so called Complementarity Determining Regions (CDRs) are transferred to a human antibody framework, resulting in a humanized antibody. Another approach is to produce completely human antibodies using recombinant technologies, which does not rely on immunization of animals to generate the specific antibody. Instead recombinant libraries comprise a huge number of pre-made antibody variants and it is likely that a library will have at least one antibody specific for any antigen. A phage display system may be used where antibody fragments are expressed, displayed, as fusions with phage coat proteins on the surface of filamentous phage particles, while the phage display system simultaneously carries the genetic information encoding the displayed molecule. Phage displaying antibody fragments specific for a particular antigen may be selected through binding to the antigen in question. Isolated phage may then be amplified and the gene encoding the selected antibody variable domains may optionally be transferred to other antibody formats as e.g. full length immunoglobulin and expressed in high amounts using appropriate vectors and host cells well known in the art. The format of displayed antibody specificities on phage particles may differ. The most commonly used formats are Fab and single chain (scFv) both containing the variable antigen binding domains of antibodies. The single chain format is composed of a variable heavy domain ($V_H$) linked to a variable light domain ($V_L$) via a flexible linker. Before use as analytical reagents, or therapeutic agents, the displayed antibody specificity is transferred to a soluble format, e.g., Fab or scFv, and analyzed as such. In later steps the antibody fragment identified to have desirable characteristics may be transferred into yet other formats such as full length antibodies.

Antibody Production Using Hybridomas

The cell fusions are accomplished by standard procedures well known to those skilled in the field of immunology. Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

An anti-oxidized LDL antibody can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

Recombinant Expression of Anti-Oxidized LDL Antibodies

Recombinant murine or chimeric murine-human or human-human antibodies that inhibit oxidized LDL can be provided according to the present invention using known techniques based on the teaching provided herein. See, e.g., Ausubel et al., eds. Current Protocols in Molecular Biology, Wiley Interscience, N.Y. (1987, 1992, 1993); and Sambrook et al. Molecular Cloning: A Laboratory Manual, Cold Spring Harbor Laboratory Press (1989).

The DNA encoding an anti-oxidized LDL antibody can be genomic DNA or cDNA which encodes at least one of the heavy chain constant region (Hc), the heavy chain variable region (Hc), the light chain variable region (Lv) and the light chain constant regions (Lc). A convenient alternative to the use of chromosomal gene fragments as the source of DNA encoding the murine V region antigen-binding segment is the use of cDNA for the construction of chimeric immunoglobulin genes, e.g., as reported by Liu et al. (Proc. Natl. Acad. Sci., USA 84:3439 (1987) and J. Immunology 139: 3521 (1987). The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1. Psoriasis Symptoms Improved in Human Patients Receiving Orticumab

In a Phase 2a study testing orticumab (a human monoclonal IgG1 antibody against an MDA-modified epitope in LDL) in patients with stable atherosclerosis, four patients enrolled were found to have a medical history of psoriasis. Three out of the four patients were administered intravenously (IV) with orticumab (an initial dose of 1245 mg, followed by 830 mg weekly×3, then 830 mg monthly×2), while the fourth patient received placebo. None of the patients were receiving concomitant medication for psoriasis during the course of this study. Of the three patients treated with orticumab, two experienced improvements in psoriasis. One patient reported an improvement after the first dose. The second patient, who was refractory to UVA/B and topical steroids, reported improvement in both elbow and knee plaques. These results showed that treatment with orticumab, an anti-inflammatory molecule, which targets oxidized forms of LDL, demonstrated therapeutic value in patients with psoriasis.

Example 2. Simulation and Actual Pharmacokinetics (PK)

The ability of orticumab to shut down macrophage pro-inflammatory activity locally in the plaque became the focus, as it was thought to be an important mechanism underlying its therapeutic activity. Initial hypothesis of using orticumab related to neutralizing oxLDL from the systemic compartment, which required 4 µg/mL=~28 nM=11 mg of orticumab to neutralize 90% systemic oxLDL. Further in vitro assays provided an insight into the minimum effective concentration of orticumab needed to achieve 50% or 90% inhibition of oxLDL-mediated cytokine release (i.e., inhibition of monocyte chemoattractant protein 1, MCP-1):

$IC_{50}$ for MCP-1 inhibition: ~10 nM=1.5 µg/mL=~4 mg $IC_{90}$ for MCP-1 inhibition: ~30-80 nM=4.5-12 µg/mL=12.4-33 mg.

The dosage (an initial dose of 1245 mg, followed by 830 mg weekly×3, then 830 mg monthly×2) in the clinical trial in Example 1, compared to the lower range (12.4 mg orticumab) as $IC_{90}$ for MCP-1 inhibition, was 67 times and 100 times greater. The dosage in the clinical trial in Example 1, compared to the higher range (33 mg orticumab) as $IC_{90}$ for MCP-1 inhibition, was 25 times and 38 times greater.

In atherosclerosis patient, it has been reported that there is an increased endothelial permeability to macromolecules, where uptake of injected macromolecules into the arterial wall is rapid and linear over time and the equilibrium against circulating blood stream is reached within 1 hour (Ross et al *NEJM* 1999).

Based on this background information, we proposed a loading dosage that would yield steady state plasma concentration of orticumab of at least 12 µg/mL for up to 96 hours in a simulation model (FIG. 1). The loading dose of 8 mg/kg (664 mg for an averaged patient of 83 kg), followed by bi-weekly to weekly 2 mg/kg (166 mg) subcutaneous (SC) dosing. This loading dose was 1.9 times less than the loading dose, and the weekly dosing was 5 times less than the weekly dosing, in Example 1.

Figure 2A:
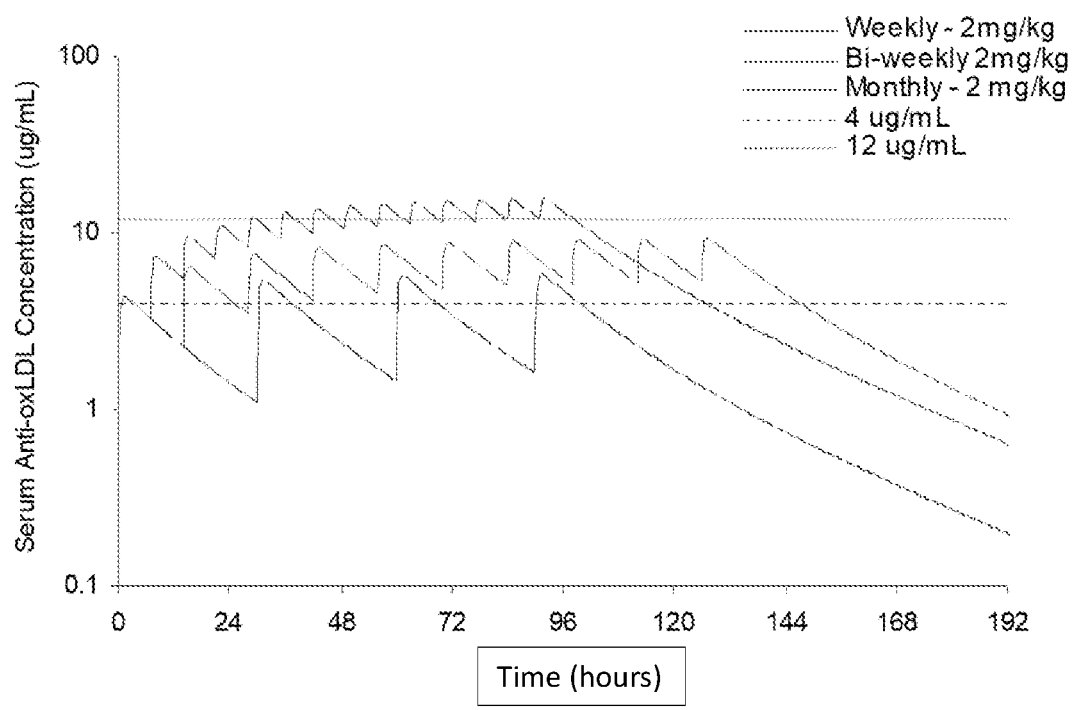
FIGS. 2A and 2B depict simulated human PK profiles based on SC dosing.
Figure 2B:
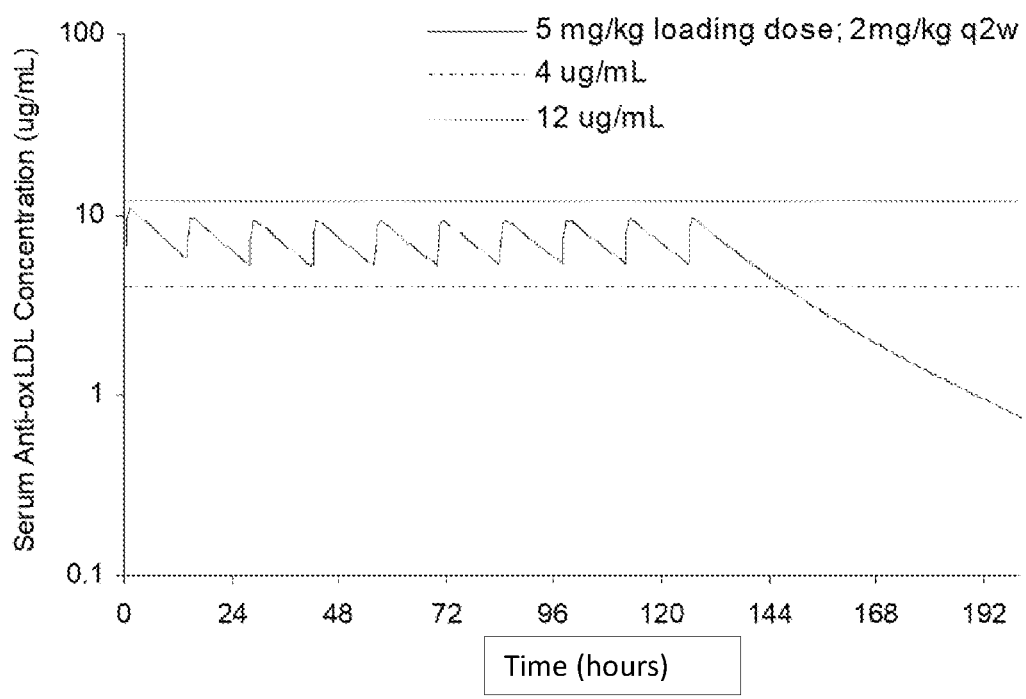

In another set of simulations based on SC dosing:

(1) Weekly dosing at 2 mg/kg (166 mg) achieved 12 µg/mL threshold between Day 2-4 (FIG. 2A);

(2) Biweekly dosing at 2 mg/kg did not achieve 12 µg/mL threshold, but did achieve 4 µg/mL threshold from Day 1-6 (FIG. 2A);

(3) Monthly dosing at 2 mg/kg did not achieve sustained exposure at the 4 µg/mL threshold (FIG. 2A);

(4) Loading Dose of 5 mg/kg (415 mg), followed by biweekly dosing at 2 mg/kg did not achieve 12 µg/mL threshold, but did maintain exposure above the 4 µg/mL through Day 6 (FIG. 2B).

In clinical trials of orticumab, Tables 1-4 below summarize the PK data.

TABLE 1

The PK data from a "FIH" trial with single dosing.

| Dose (mg/kg) | Route of Admin | $C_{max}$ (µg/mL) | C ≥ 1 µg/mL | C ≥ 4 µg/mL | C ≥ 12 µg/mL |
|---|---|---|---|---|---|
| 1.25 | SC | 2.99 | Day 28 | Not achieved | Not achieved |
| 1.25 | IV | 20.6 | Day 28 | Day 3 (<Day 7) | 11 hours |
| 5 | IV | 105 | Day 56 | Day 14 | Day 3 |
| 15 | IV | 286 | Day 70* | Day 42 | Day 28 |

*Last day of assessment

TABLE 2

The PK data from a "FIH" trial with multiple dosing.

| Dose (mg/kg) | Route of Admin | $C_{max}$ (µg/mL) | C ≥ 1 µg/mL | C ≥ 4 µg/mL | C ≥ 12 µg/mL |
|---|---|---|---|---|---|
| 1.25 | SC | 1.24 | Day 42 | Not achieved | Not achieved |
| 1.25 | IV | 29.6 | Day 70 | Day 28 | Day 23 |
| 5 | IV | 105 | Day 91* | Day 56 | Day 35 |
| 15 | IV | 303 | Day 91* | Day 91 | Day 56 |

*Last day of assessment

TABLE 3

The PK data from a "Ph1" trial with single dosing comparing subcutaneous (SC) and intravenous (IV) administration.

| Dose (mg) | Route of Admin | $C_{max}$ (µg/mL) | C ≥ 1 µg/mL | C ≥ 4 µg/mL | C ≥ 12 µg/mL |
|---|---|---|---|---|---|
| 360 | SC | 9.15 | Day 43 | Day 15 | Not achieved |
| 360 | SC 70-90 days after IV dosing | 15.1 | Day 57 | Day 15 | Day 8 |
| 360 | IV | 84.3 | Day 57* | Day 15 | Day 8 |

*Last day of assessment

TABLE 4

The PK data from a "Ph2" trial.

| Dose Group | Route of Admin | $C_{max}$ (µg/mL) D1 | C ≥ D78* | C ≥ 1 µg/mL | C ≥ 4 µg/mL | C ≥ 12 µg/mL |
|---|---|---|---|---|---|---|
| Single Dose | IV | 297 | N/A | Day 106 | Day 50 | Day 22 |
| Multiple Dose | IV | 286 | 197 | Day 169 | Day 141 | Day 106 |

Dosing days: D1, 8, 15, 22, 50, 78
*Last day of dosing

Cmax, Single Dose at 1.25 mg/kg: 1.25 mg/kg=104 mg, which was 6.9 times greater max exposure with IV vs SC admin (½-life is 20 days for both); SC dose does not reach threshold of 4-12 µg/mL.

Cmax, Single Dose at 360 mg: 360 mg=4.34 mg/kg (3.5 times FIH study), 9.2 times greater max exposure with IV vs SC admin (½-life is 33.5 vs 24.3 days, IV vs SC); SC dose falls within range of 4-12 µg/mL.

As a result, based on the simulated and actual PK data, 8 mg/kg (664 mg) is optimal, but 5 mg/kg (415 mg) is likely sufficient. Based on the ½-life of a single dose in the clinical studies (i.e., 24 days with a single SC dose of 360 mg), monthly dosing is reasonable.

Figure 3:
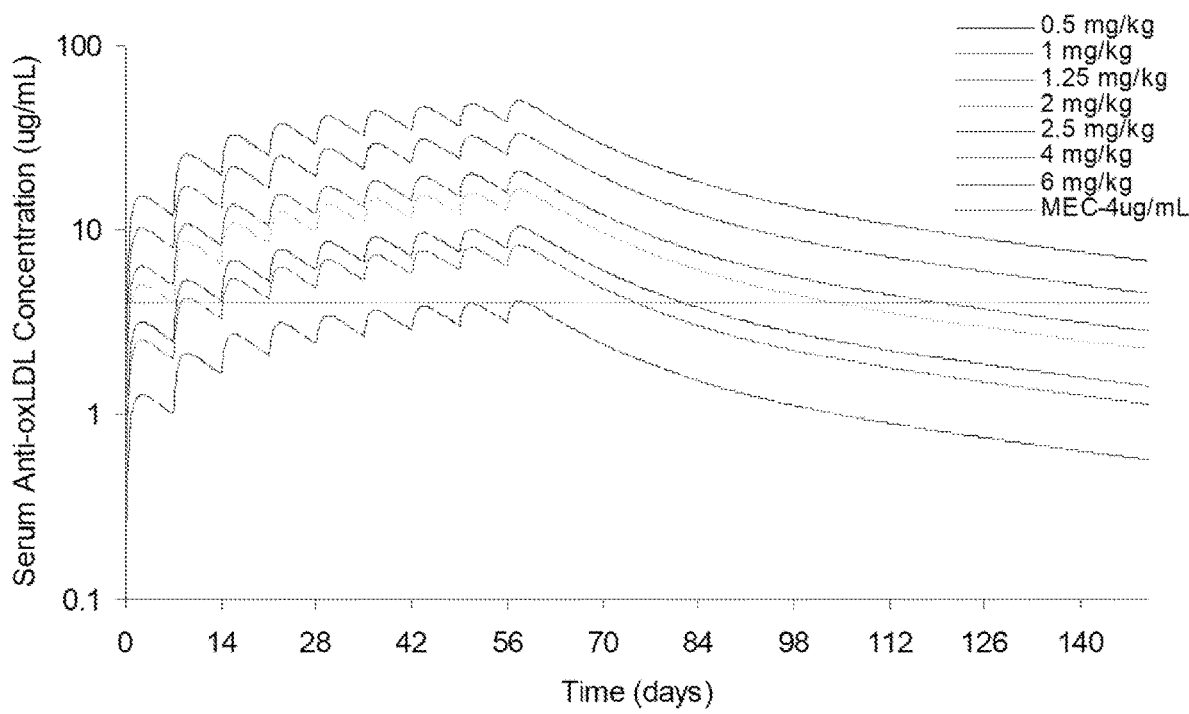
FIG. 3 depicts the simulated human PK profiles after weekly SC dosing, using PK parameters from Phase I data. The solid lines in the graph from low to high represent dosages at 0.5, 1, 1.25, 2, 2.5, 4 or 6 mg/kg.

In another set of studies of orticumab:

(1) Weekly SC dose of 1 mg/kg and above maintained concentrations above 4 µg/mL at steady state. FIG. 3 depicts the simulated human PK profiles after weekly SC dosing, using PK parameters from Phase I data. Bioavailability after SC dose is 70%.

Figure 4:
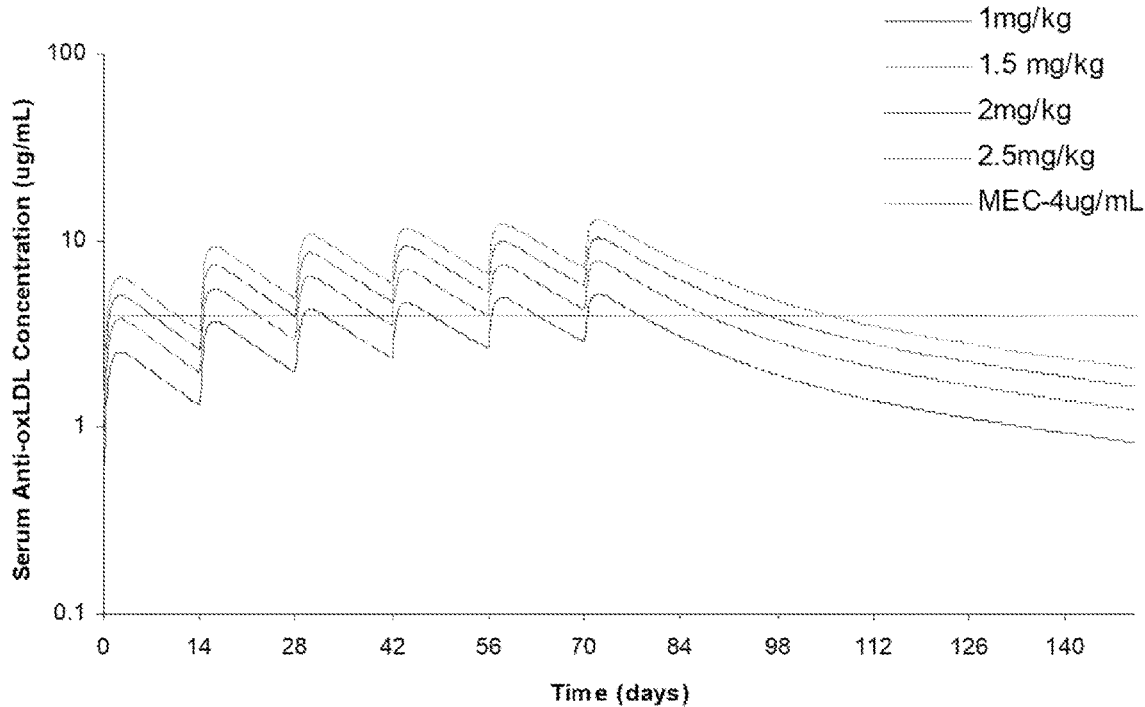
FIG. 4 depicts the simulated human PK profiles after bi-weekly SC dosing, using PK parameters from Phase I data. The solid lines in the graph from low to high represent dosages at 1, 1.5, 2 or 2.5 mg/kg.

(2) Bi-weekly SC dose of 1.5 mg/kg and above maintained concentrations above 4 µg/mL at steady state. FIG. 4 depicts the simulated human PK profiles after bi-weekly SC dosing, using PK parameters from Phase I data.

Figure 5:
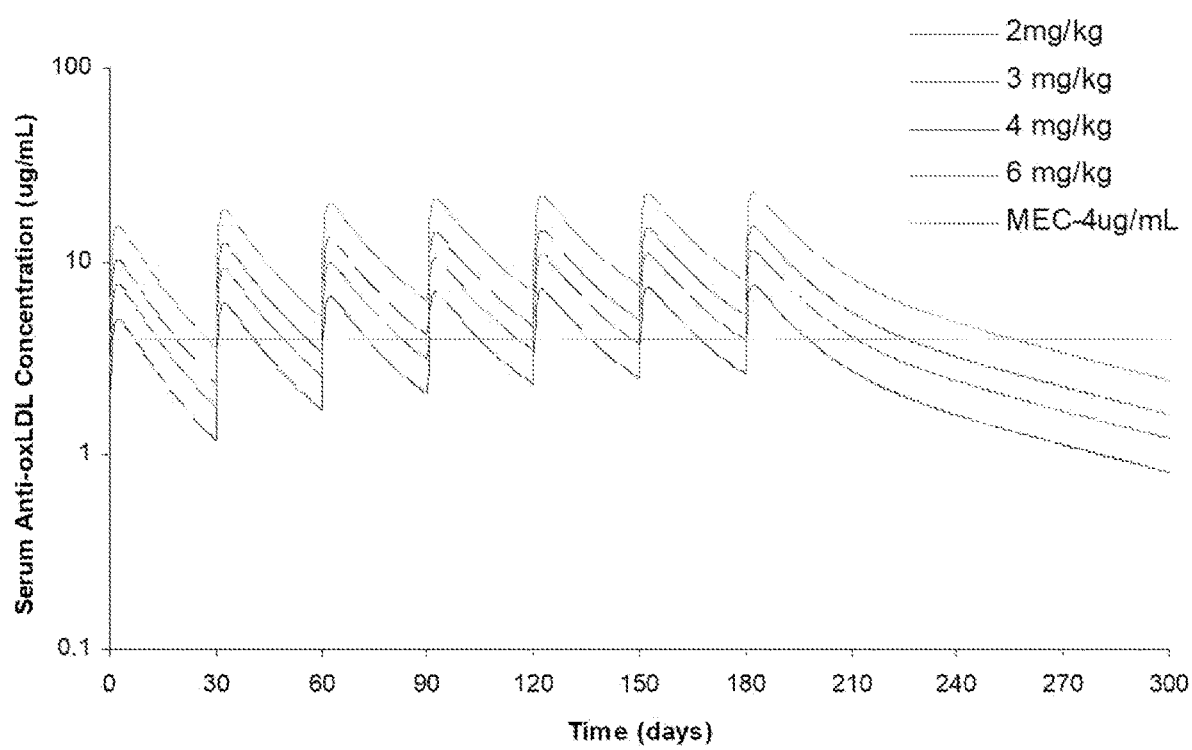
FIG. 5 depicts the simulated human PK profiles after monthly SC dosing, using parameters from Phase I data. The solid lines in the graph from low to high represent dosages at 2, 3, 4 or 6 mg/kg.

(3) Monthly SC dose of ~3 to 4 mg/kg and above maintained concentrations above 4 µg/mL. FIG. 5 depicts the simulated human PK profiles after monthly SC dosing, using parameters from Phase I data.

Based on simulated PK data, and targeting a plasma concentration of 12 µg/mL threshold for maximum chance of success, weekly dosing should be no less than 2 mg/kg (166 mg); 4 mg/kg (332 mg) would be preferable; biweekly dosing must be >2.5 mg/kg (208 mg); higher doses were not simulated; and monthly dosing should be 6 mg/kg (498 mg). In some embodiments, final recommendation is 500 mg, monthly via SC injection. Monthly dosing of 500 mg each month can be administered 12 doses over a 12-month dosing regimen, or 3 doses over a 3-month dosing regimen. Monthly dosing of 330 mg each month (to meet the minimum 4 µg/mL plasma concentration threshold) can be administered 12 doses over a 12-month dosing regimen, or 3 doses over a 3-month dosing regimen.

Example 3. A Multi-Center, Randomized, Double-Blind, Placebo-Controlled Phase-Two Study to Evaluate the Efficacy, Safety, Tolerability, Pharmacokinetics and Pharmacodynamics of Monthly Administered Orticumab in Patients with Chronic Plaque Psoriasis and Coronary Artery Disease Patients with psoriasis have accelerated atherosclerosis and are at increased risk of developing cardiovascular disease (CVD). Both psoriasis and atherosclerosis share common inflammatory mediators, such as IL-6, TNFα, and C-reactive protein (CRP).

It has been reported that MDA-LDL and oxLDL are significantly increased in patients with psoriasis. Importantly, oxLDL was found specifically in psoriatic skin lesions, whereas non-lesional skin from the same patients was free of oxLDL. Furthermore, antibodies against oxLDL are thought to correlate with disease severity (Psoriasis Area and Severity Index [PASI] score), as well as with total cholesterol, LDL, oxLDL, and CRP, in psoriasis patients. However, it is unknown how the administration of autoantibodies to oxLDL might affect psoriasis, prior to Applicant's invention.

The primary objective of the study is to evaluate the superiority of orticumab over placebo with respect to reduction in psoriasis area of involvement, severity and improvement. The secondary objectives include evaluate the safety and tolerability of subcutaneous doses of orticumab in adult subjects with moderate plaque psoriasis; evaluate the efficacy of subcutaneous doses of orticumab in adult subjects with moderate plaque psoriasis; evaluate the change of psoriasis severity and area(s) of involvement in subjects with moderate plaque psoriasis; evaluate the change in coronary artery inflammation by mapping spatial changes of perivascular fat attenuation on coronary computed tomography angiography (CCTA) in subjects with moderate plaque psoriasis; evaluate changes in coronary artery plaque volume, assessed by CCTA in subjects with moderate plaque psoriasis; evaluate pharmacokinetics of orticumab in adults with moderate plaque psoriasis with sparse blood sampling; to evaluate the plasma concentration vs. pharmacodynamic effect of orticumab in subjects with moderate plaque psoriasis.

The primary outcome measures include the percentage of subjects with psoriasis achieving treatment success (clear=0 or almost clear=1) and greater than or equal to (>=) 2 Point Improvement from Baseline on the 5-point static Investigator's Global Assessment modified 2011 version (sIGA) (Baseline to Week 16).

The secondary outcome measures include the percentage of subjects who achieve a reduction in PASI score of at least 75% (PASI 75) from baseline to Week 16; the percentage of subjects achieving PASI90 [Time Frame: the achievement of at least 90% reduction from baseline PASI score (PASI90 response) at weeks 4, 8, 12, 16, 20, 24, 28, 32, 36, 40, 44, 48 and 52+/−3 days]; the percentage of participants achieving PASI75 [Time Frame: the achievement of at least 75% reduction from baseline PASI score (PASI75 response) at weeks 4, 8, 12, 16 20, 24, 28, 32, 36, 40, 44, 48 and 52+/−3 days]; the percentage of participants achieving 50 percent reduction from baseline PASI score (PASI50 Response) at weeks 2, 4, 6, 8, 8, 10, 12 and 16+/−3 days [Time Frame: Weeks 4, 8, 12, 16, 20, 24, 28, 32, 36, 40, 44, 48 and 52+/−3 days]; the mean change from baseline in PASI Score at weeks 4, 8, 12, 16, 20, 24, 28, 32, 36, 40, 44, 48 and 52+/−3 days [Time Frame: Baseline, Weeks 4, 8, 12, 16, 20, 24, 28, 32, 36, 40, 44, 48 and 52+/−3 days]; the mean change in the sIGA modified 2011 version at weeks 4, 8, 12, 16, 20, 24, 28, 32, 36, 40, 44, 48 and 52+/−3 days [Time Frame: Weeks 4, 8, 12, 16, 20, 24, 28, 32, 36, 40, 44, 48 and 52+/−3 days]; the percentage of subjects achieving greater than or equal to (>=) 2 point improvement from baseline for participants with a score of 3 at baseline in the sIGA modified 2011 version at weeks 4, 8, 12, 16, 20, 24, 28, 32, 36, 40, 44, 48 and 52+/−3 days [Time Frame: Weeks 4, 8, 12 and 16, 20, 24, 28, 32, 36, 40, 44, 48 and 52+/−3 days]; the percentage of subjects achieving clear=0 or almost clear=1 clear on the 5 point sIGA for participants with a score of 3 at baseline at weeks 4, 8, 12, 16, 20, 24, 28, 32, 36, 40, 44, 48 and 52+/−3 days [Time Frame: Weeks 2, 4, 8, 12 and 16, 20, 24, 28, 32, 36, 40, 44, 48 and 52+/−3 days]; the percentage of subjects achieving clear=0 or almost clear=1 and greater than or equal to (>=) 2 point improvement from baseline on the 5 point sIGA for participants with a score of 3 at baseline at weeks 4, 8, 12, 16, 20, 24, 28, 32, 36, 40, 44, 48 and 52+/−3 days [Time Frame: Weeks 4, 8, 12 and 16, 20, 24, 28, 32, 36, 40, 44, 48 and 52+/−3 days]; the mean change from baseline in the Itch Numerical Rating Scale Score at weeks 4, 8, 12, 16, 20, 24, 28, 32, 36, 40, 44, 48 and 52+/−3 days [Time Frame: Baseline, Weeks 4, 8, 12, 16, 20, 24, 28, 32, 36, 40, 44, 48 and 52+/−3 days]; the change in the Dermatology Life Quality Index (DLQI) mean change from baseline to weeks 16 and 52+/−3 days in the DLQI Total Score [Time Frame: Baseline, Weeks 16 and 52+/−3 days]; the change in body surface area (BSA) mean from baseline to weeks 16 and 52+/−3 days in the BSA [Time Frame: Baseline, Weeks 16 and 52+/−3 days]; the change in cholesterol and lipid profile (mean change from baseline to weeks 16 and 52+/−3 days); Change in High-sensitivity C-reactive protein (Mean change From Baseline to Weeks 16 and 52+/−3 days); the change in oxidized-modified lipids; the change in LDL, Lipoprotein(a), oxLDL and oxHDL (mean change from baseline to weeks 16 and 52+/−3 days); the number and percent of participants with one or more treatment emergent Adverse Events (AEs) or Any Serious AEs [Time Frame: Baseline up to 52 weeks+/−3 days]; the change in hemodynamic and EKG parameters [Time Frame Baseline up to 52 weeks+/−3 days]; the change in blood chemistry and hematology [Time Frame Baseline up to 52 weeks+/−3 days]; the effect on weight and BMI [Time Frame: Baseline up to 52 weeks+/−3 days]; the change in physical examination [Time Frame: Baseline up to 52 weeks+/−3 days];

Exploratory measures include the change in coronary artery perivascular fat attenuation index (FAI) measured by CT angiography for subjects with −190 Hounsfield units to −30 Hounsfield units at screening; the mean change from screening to week 52+/−3 days [Time Frame: Screening to week 52+/−3 days] around the proximal right coronary, the proximal left anterior descending artery and left circumflex artery; the change in coronary artery perivascular fat attenuation index (FAI) measured by CT angiography for subjects with −30 to −70 Hounsfield units (HU) (low group) at screening; the mean change from screening to week 52+/−3 days [Time Frame: Screening to week 52+/−3 days] around the proximal right coronary, the proximal left anterior descending artery and left circumflex artery; the change in coronary artery perivascular fat attenuation index (FAI) measured by CT angiography for subjects with −71 Hounsfield units (HU) to −110 Hounsfield units (HU) (medium group) at screening; the mean change from Screening to week 52+/−3 days [Time Frame: Screening to week 52+/−3 days] around the proximal right coronary, the proximal left anterior descending artery and left circumflex artery; the change in coronary artery perivascular fat attenuation index (FAI) measured by CT angiography for subjects with >110 Hounsfield units (HU) to −190 Hounsfield units (HU) (high group) at screening; the mean change from Screening to week 52+/−3 days [Time Frame: Screening to week 52+/−3 days] around the proximal right coronary, the proximal left anterior descending artery and left circumflex artery; the change in coronary artery perivascular fat attenuation index (FAI) measured by CT angiography for subjects with <70 Hounsfield units (HU) and in those with >70 Hounsfield units (HU) (high group) at screening; the mean change from screening to week 52+/−3 days [Time Frame: Screening to week 52+/−3 days] around the proximal right coronary, the proximal left anterior descending artery and left circumflex artery; the change in noncalcified and low attenuation coronary artery plaque volume, assessed by coronary computed tomographic angiography (CCTA), as an indicator of coronary atherosclerosis; the mean change from screening to week 52+/−3 days [Time Frame: Screening to week 52+/−3 days]; the change in coronary artery calcification score; the mean change from screening to week 52+/−3 days [Time Frame: Screening to week 52+/−3 days]; the change in total plaque volume (noncalcified plaque plus dense calcium plaque); the mean change from screening to week 52+/−3 days [Time Frame: Screening to week 52+/−3 days]; the change in fibrous plaque volume; the mean change from screening to week 52+/−3 days [Time Frame: Screening to week 52+/−3 days]; the change in low-attenuation plaque volume and fibrous-fatty plaque volume; the mean change from screening to week 52+/−3 days [Time Frame: Screening to week 52+/−3 days]; and the change in dense-calcified plaque burden (DCB); the change in non-calcified plaque burden (NCB).

Study Design

Following the screening period (Table 5), subjects will be enrolled into one of two groups, 330 mg/month subcutaneous (sc) (1.1 ml×2 sc injections) of orticumab or matching placebo. Each subject will receive up to 48 weeks of treatment with monthly orticumab or placebo. Subjects will be randomized equally to orticumab or matching placebo in each group (approximately 50 subjects orticumab and 50 subjects on matching placebo). Single use prefilled vials and matching placebo will be provided by Abcentra, LLC. Participants will receive sub-cutaneous orticumab or matching placebo. An estimated 100 participants are planned for enrollment: male and female subjects with moderate chronic plaque psoriasis—50 subjects in group one and 50 subjects in group two.

Every effort will be made to randomize at least 20 females in each group and effort will be made to randomize equal numbers of subjects on statins to each treatment group. In addition, the randomization will be stratified by Hounsfield unit measures on screening computerized tomographic angiography so that subjects will be randomized approximately equally to high, medium, and low groups across both treatment groups.

Planned treatments are monthly subcutaneous injections of 330 mg sc (1.1 ml×2 sc injections) of orticumab or matching placebo. Blinded safety, tolerability, and efficacy data will be reviewed by the Internal Safety Review Committee (ISRC) every 2 weeks up to 16 weeks starting after the first five subjects have completed 2 weeks of dosing and then every month (+/−1 week) thereafter or sooner as necessary.

From week 16 to week 52 (Table 6) blinded safety, tolerability, and efficacy data will be reviewed by the Internal Safety Review Committee (ISRC) at least every month or sooner as needed up to 52 weeks.

A safety monitoring plan will be completed prior to study start and will be followed until the last subject has completed their last visit. Stopping criteria will be utilized in this study based on laboratory values, vital signs, physical examination, electrocardiograms (EKGs), and adverse events (AEs).

Rescue Medications—After week 16 any subject in the opinion of the investigator who requires medication to treat their psoriasis (in addition to their current blinded treatment) may be allowed to take topical corticosteroids, Vitamin D analogues, topical retinoids, keratolytics, coal tar, calcipotriol dithranol or any prescription or non-prescription topical psoriasis treatment in any combination that in the investigator's medical judgement will be safe and potentially effective in treating the subject's psoriasis for whatever period of time during the study may be deemed necessary. The investigator and qualified staff must supervise the administration of these medications and a related log will be provided by the sponsor for sites to complete.

The primary efficacy analysis will be conducted to assess the efficacy of orticumab once all subjects have completed 16 weeks of participation in their group (i.e., either fully completed 16 weeks of treatment or withdrawn prematurely). The purpose of the week 16 analysis will be to provide the sponsor with an early indication of efficacy and safety from the trial, with minimal implication for altering the conduct of the study. Investigators and subjects will remain blind to treatment assignment and to the results of the unblinded efficacy and safety assessment.

Participation in each group will continue during the conduct of the week 16 analysis since it will take time for all 16-week data to be retrieved, all data queries resolved, the database finalized, unblinded and analyzed. While the study is not planned to be stopped for efficacy, the study may be stopped for futility or the sample size may be revised, based on the results of the week 16 analysis. Details of the analyses to be performed will be made available in the Statistical Analysis Plan (SAP).

Study Population

Inclusion

Males or females aged 18-75 years at time of consent.

Female subjects who agree to use one of the following methods of contraception during participation in the study and for 4 months following the last dose of study drug, unless they are postmenopausal (defined as no menses for 12 months without an alternative medical cause and confirmed by follicular stimulation hormone [FSH]>40 mIU/mL) and/or surgically sterile (hysterectomy or bilateral oophorectomy):

Combined (estrogen and progestogen containing) oral, intravaginal, or transdermal hormonal contraception associated with inhibition of ovulation Oral, injectable, or implantable progestogen-only hormonal contraception associated with inhibition of ovulation Intrauterine device Intrauterine hormone-releasing system Bilateral tubal ligation/occlusion Vasectomized partner Sexual abstinence (no sexual intercourse)

Males with female partners of childbearing potential must agree to a double barrier method if they become sexually active during the study and for 4 months following the study. Male subjects must not donate sperm for 4 months following their participation in the study.

Must have previously been a candidate for or have received topical and/or phototherapy Diagnosis of plaque psoriasis for at least 6 months prior to screening. The patients must meet all the following criterion:

Stable plaque psoriasis at screening and randomization

Coverage of the body surface area (BSA) of between 3% and 10% with plaques at screening and baseline PASI≥4.5 but lower than PASI 12 sIGA score of 3—moderate (5-point scale) at screening and baseline

Screening coronary artery perivascular fat attenuation Index (FAI) measured by CT angiography within the range of −190 Hounsfield units to −30 Hounsfield units.

Able to communicate well with the investigator and understand and comply with the requirements of the study. Understand and sign the written informed consent.

Vital signs must be within the following ranges and stable.

Systolic blood pressure, 90-150 mm Hg

Diastolic blood pressure, 50-90 mm Hg

Pulse rate, 40-100 bpm

Blood pressure (≤150/90 mmHg); may include stable dose (≥45 days of use) of up to two anti-hypertensive medications that are intended to remain at a stable dose during the protocol.

Results of screening clinical laboratory tests (CBC with differential and platelets and chemistry profile) must be within normal range or, if outside of the normal range, must be accepted by the investigator and sponsor as not clinically significant.

Subjects may be on stable doses of chronic concomitant medications while participating in the study so long as these medications do not interfere with the interpretation of primary and key secondary endpoints and are not listed as excluded in the protocol. Stable dosing is defined as no changes in the type of medication for at least 60 days prior to Day 1 (baseline) and no changes in dose for at least 45 days prior to Day 1 (baseline) and no changes in concomitant medications are planned during the course of the study.

Subjects who are on stable lipid lowering therapy or on a lipid modifying diet prior to baseline may be included so long as there are no plans to change their lipid lowering therapy or diet during the trial.

Exclusion

Any of the nonplaque forms of psoriasis: erythrodermic, guttate, or pustular at screening or baseline Subjects with scalp, palmar or plantar psoriasis only.

Severe psoriasis PASI>10

Have drug-induced psoriasis (e.g. new onset or exacerbation of psoriasis from beta blockers, calcium channel blockers, or lithium).

Treatment with other biological therapies or immunosuppressive agents such as but not limited to cyclosporine, mycophenolate, pimecrolimus, or tacrolimus within the 3 months prior to baseline.

The following minimum washout periods will be required for patients to be eligible to participate in the trial.

3-months washout prior to screening for biologic therapies such as etanercept, adalimumab, infliximab or other biologics 1-month washout prior to screening for immunosuppressants including but not limited to cyclosporine, mycophenolate, tacrolimus, and any systemic immunosuppressants including but not limited to methotrexate, azathioprine, thioguanine prednisone, mercaptopurine, hydroxyurea and mycophenolate mofetil 2-week washout prior to screening for the following: systemic retinoids, phototherapy or photochemotherapy, high potency topical corticosteroids, "alternative medicine" treatments for psoriasis, prolonged sun exposure or tanning bed use, which may in the opinion of the investigator, modify disease activity.

Topical treatment with agents such as but not limited to topical corticosteroids, Vitamin D analogues and topical retinoids, keratolytics, coal tar and dithranol within 1-week prior to commencement of study treatment and for the duration of the study History of allergy/hypersensitivity to a systemically administered biologic agent or its excipients.

Subjects with a history of hypersensitivity or allergies to orticumab or any of the contents of the SC formulation Participation in any clinical study with an investigational drug/device within 2 months prior to the first day of dosing.

Has an underlying condition that predisposes to infections (e.g. immunodeficiency, hi story of poorly controlled diabetes, splenectomy).

Is an immediate family member, study site employee, or is in a dependent relationship with a study site employee involved in conduct of this study (e.g., spouse, parent, child, sibling), or may consent under duress.

Chronic or acute hepatitis B and C, or carrier status. Patient with anti-HBc Ab and undetectable anti-HBs Ab should also be excluded.

Positive history for human immunodeficiency virus (HIV)

History of tuberculosis, tuberculosis or a positive tuberculin skin test (TST) for tuberculosis. Subjects previously received BCG vaccination can participate in the study after showing negative responses in Interferon-Gamma Release Assays (IGRA).

History of recurring infections

History of malignancy in the past 5 years or suspicion of active malignant disease except treated cutaneous squamous cell or basal cell carcinoma and treated carcinoma in situ of the cervix uteri.

Intake of restricted medications or other drugs considered likely to interfere with the safe conduct of the study Diagnosis of Major Depressive Disorder, schizophrenia, bipolar disorder, personality disorder or other DSM-V disorders which the investigator believes will interfere significantly with study compliance.

Suicidal ideation within 1 year prior to the Screening Visit

Illness that in the opinion of the investigator was clinically significant in the 8 weeks before screening.

Liver, renal, pulmonary, cardiac, oncologic, or GI disease that in the opinion of the investigator is considered clinically significant or that may interfere with the interpretation of safety laboratories, physical examination or the interpretation of potential adverse events Liver disease or liver injury as indicated by abnormal liver function tests, SGOT (AST), alkaline phosphatase, or serum bilirubin (>1.5×ULN for any of these tests) or history of hepatic cirrhosis.

History or presence of impaired renal function as indicated by clinically significantly abnormal creatinine, BUN, or urinary constituents (e.g., albuminuria) or moderate to severe renal dysfunction as defined by the Cockroft Gault equation (GFR<60 mL/min).

Significant history of abuse of drugs or solvents in the year before screening or a positive Drugs of Abuse (DOA) test at screening;

Subjects with legitimate medically supervised uses of drugs that might otherwise be considered drugs of abuse can be enrolled at the discretion of the investigator after the investigator documents the justification for enrollment and reviews this with the sponsor;

History of alcohol abuse in the past year before screening or currently drinks in excess of 21 units per week (3 servings or units/day).

Exclusions related to coronary computed tomographic angiography;

Prior coronary artery surgery including stint placement;

Conditions that increase the risk of performing the procedure (estimated glomerular filtration rate <60 mL/min/1.73 m2 or known allergy to iodinated contrast medium);

Factors that make the procedure technically impractical (weight >136 kg, inability to hold the breath for 10 seconds, a current or prior (within the last year) diagnosis of tachycardia or irregular heart rhythm [e.g., atrial fibrillation).

Subject is, in the opinion of the Investigator, not suitable to participate in the study.

Clinically significant blood loss or blood donation >500 mL within 3 months.

Inadequate venous access.

Study drug: orticumab is a fully humanized recombinant monoclonal antibody directed against the specific oxidized low-density lipoprotein, malondialdehyde-modified human ApoB100. It is intended to act an anti-inflammatory in subjects with Plaque Psoriasis and Coronary Artery Inflammation.

Study duration: the study will take approximately 14.5 months and includes a 4-week screening period, 48 weeks drug or matching placebo administration, one end of treatment evaluation visit (week 52+/−3 days) and 2 weeks for subjects in each group to return for their follow-up visit after their last treatment visit.

Subject duration: subjects will each take approximately 58 weeks (14.5 months) to complete all study visits including Screening (4 weeks), Treatment (48 weeks), one end of treatment evaluation visit (week 52+/−3 days) and Follow Up (2 weeks).

Study Procedures:

Screening (Day minus 30 to Day 1) (also see Table 5 Schedule of Assessments). Informed consent will be obtained, and subjects will undergo procedures to determine eligibility. Eligible male and female subjects who give informed consent to participate in the trial and who have met all screening inclusion criteria and have no screening exclusions will undergo coronary computed tomographic angiography during the screening period which will be used as their baseline reading.

Baseline (Day 1, Week 1, Visit 1)

Eligible male and female subjects will be randomly assigned to 330 mg orticumab or matching placebo after reconfirmation of eligibility and baseline efficacy and safety assessments on Day 1. Subjects will receive treatment with 330 mg orticumab administered as two 1.1 ml sc injections or matching placebo monthly for 48 weeks+/−3 days of treatment. Safety and tolerability will be monitored by physical examinations, assessments of AEs and concomitant medications, assessments of suicidality, vital signs, safety laboratory tests (hematology [including coagulation], chemistry, urinalysis and ECGs.

The following measures will be obtained prior to dosing at the baseline visit (also see Table 5 Schedule of Assessments).

Psoriasis Area and Severity Index—PASI
Percent psoriasis coverage of the body surface area (BSA)
Investigator Global Assessment (sIGA)
Patient's Global Assessment (PtGA)
Clinic-Based Itch Numerical Rating Scale (INRS)
Dermatology Life Quality Index—DLQI
Completed, read and interpreted screening coronary computed tomographic angiography
Standardized digital photographs of Body Surface Areas (excluding head and groin)—Selected Sites
Psoriatic Arthritis Questionnaire.

Treatment Phase [Week 1 to Week 16 (Visits 1-9)]

Safety, tolerability and efficacy will be reviewed by the Internal Safety Review Committee (ISRC) for all subjects enrolled after the first five subjects have completed 2 weeks of treatment and every month+/−1 week thereafter or sooner as needed. Individual and study stopping criteria will be utilized in this study based on laboratory values, vital signs, electrocardiograms (ECGs), adverse events and physical examination (AEs).

The following measures will be obtained at weeks 4, 8, 12 and 16+/−3 days (also see Table 5 Schedule of Assessments).

Psoriasis Area and Severity Index—PASI
Investigator Global Assessment (sIGA)
Clinic-Based Itch Numerical Rating Scale (INRS)

The following will also be obtained at week 16+/−3 days (also see Table 5 Schedule of Assessments).

Patient's Global Assessment (PtGA)
Dermatology Life Quality Index—DLQI
Body Surface Area Affected by Psoriasis (%)
Drug Accountability
Physical Examination
Pregnancy Test
Laboratory Evaluations
Triplicate 12-Lead ECG
Standardized digital photographs of Body Surface Areas (excluding head and groin)—Selected Sites
Psoriatic Arthritis Questionnaire Treatment Phase [Week 20 to Week 52 (Visits 10-19)]

Safety, tolerability and efficacy will be reviewed at least monthly by the Internal Safety Review Committee (ISRC) for all subjects enrolled. Individual and study stopping criteria will be utilized in this study based on laboratory values, vital signs, electrocardiograms (ECGs), and adverse events (AEs).

The following measures will be obtained at weeks 20, 24, 28, 32, 36, 40, 44, 48 and 52+/−3 days (also see Table 6 Schedule of Assessments).

Psoriasis Area and Severity Index—PASI
Investigator Global Assessment (sIGA)
Clinic-Based Itch Numerical Rating Scale (INRS)
Body Surface Area Affected by Psoriasis (%)
Drug Accountability The following will also be obtained at weeks 28, 36 and 52+/−3 days (also see Table 6 Schedule of Assessments).

Patient's Global Assessment (PtGA)
Physical Examination
Laboratory Evaluations
Triplicate 12-Lead ECG The following will also be obtained at week 52+/−3 days (also see Table 6 Schedule of Assessments).

Dermatology Life Quality Index—DLQI
Pregnancy Test
Coronary computed tomographic angiography (CCTA)
Standardized digital photographs of Body Surface Areas (excluding head and groin)—Selected Sites
Psoriatic Arthritis Questionnaire Follow-up Visit—post screening Week 54 (Visit 20)

The following will be obtained at week 54+/−3 days (also see Table 5 Schedule of Assessments): Vital Signs.

Statistical Methods

Sample size considerations:

In prior studies, placebo response rates for the primary endpoint range from 0% to 10%. Assuming a true placebo response rate of 10% and based on the use of a two-sided, two-sample comparison of binomial proportions at the alpha=0.05 level of significance, a sample size of 100 subjects (50 subjects per arm) will provide 90% power to detect an improvement of 27 percentage points, i.e., a true response rate of 37% in the active arm. No formal statistical assessment, in terms of sample size, was conducted for population PK estimates.

Every effort will be made to distribute subjects on lipid lowering therapies evenly between placebo and active treatment arms.

Primary Efficacy Analysis:

The primary analysis, as well as all other efficacy analyses, will be conducted in the Intent-to-Treat (ITT) analysis set, defined as all randomized subjects. The active and placebo groups will be compared using the two-sided Cochran-Mantel-Haenszel statistic (stratified by the randomization stratification variable) at the alpha=0.05 level of significance.

Key Secondary Efficacy Analysis:

If the primary efficacy analysis is statistically significant (p<0.05), then the key secondary endpoint will be analyzed using the Cochran-Mantel-Haenszel statistic (stratified by the randomization stratification variable) at the alpha=0.05 (two-sided) level of significance. However, if the primary analysis is not statistically significant, the results of the key secondary analysis will be exploratory rather than confirmatory.

Data Presentation/Descriptive Statistics:

All demographic, safety, PK and efficacy data will be listed and summarized in tabular format and by descriptive statistics as appropriate. Pharmacokinetic and efficacy data will also be displayed graphically as appropriate. The paired comparisons of PK and efficacy parameters will also be reported. Exploratory analysis may be performed for comparison between groups.

Statistical Models:

In general, any statistical model will be summarized using estimates and confidence intervals for the model effects. Geometric mean rations and interval estimates will be reported for Ctrough compared across time points.

Outcome Measures

Psoriasis Area and Severity Index (PASI)—The PASI combines assessments of 4 body areas: the head and neck (H), the upper limbs (UL), the trunk (T) and the lower limbs (LL). The percentage of skin affected by psoriasis in each area is given a numerical score representing the Percentage involved: 1 (0-9%), 2 (10-29%), 3 (30-49%), 4 (50-69%), 5 (70-89%) or 6 (90-100%). Within each area (H, UL, T, LL) the severity of 3 plaque signs—erythema (E), thickness/induration (I) and desquamation/scaling (D)—is assessed on a 5-point scale: 0 (none), 1 (mild), 2 (moderate), 3 (severe) or 4 (very severe).

The assessment of lesion severity and area affected are combined into single score. The final PASI will be=sum of severity parameters for each region×area score×weight of region (where head: 0.1, arms: 0.2, body: 0.3, legs: 0.4); total possible score range: 0=no disease to 72=maximal disease.

The maximum PASI score that can be measured will be <72 since the PASI assessment will exclude scalp, palms, finger nails, soles, and toe nails.

Video training will be mandatory for trial investigators involved in this assessment The final PASI score will be calculated using the following formula:

$$PASI = 0.1(EH+IH+HH)AH + 0.2(EUL+IUL+HUL)AUL + 0.3(ET+IT+HT)AT + 0.4(ELL+ILL+HLL)ALL$$

A reduction in the PASI score from baseline indicates improvement. The percentage change will be calculated by subtracting the weeks 16 and 52 values from the baseline values. The percentage change will be calculated for each entire treatment group (not for each participant). A positive percentage change from baseline will indicate improvement.

Training will be mandatory for trial investigators involved in this assessment

Body Surface Area—Scored as the percentage body area affected by psoriasis; 0-100%. A commonly used method to estimate the body surface area of psoriatic lesions is the "rule of nines", which was originally developed for estimating the surface area of burns. It is defined as 9% coverage for the head and neck, 9% for each arm, 9% for the anterior and posterior legs, and 9% for each of 4 trunk quadrants, leaving 1% for the genitalia. The BSA can also be estimated by the number of a patient's hand areas affected, on the assumption that one "handprint" reflects approximately 1% of BSA.

Training will be mandatory for trial investigators involved in this assessment

Investigator Global Assessment—The IGA is a 5-category scale including "0=clear", "1=almost clear", "2=mild", "3=moderate" or "4=severe" indicating the physician's overall assessment of the psoriasis severity focusing on induration, erythema and scaling. Treatment success of "clear" or "almost clear" consists of no signs of psoriasis or normal to pink coloration of lesions, no thickening of the plaque, and none to minimal focal scaling. The IGA captures and categorizes the global assessment of all clinical signs and symptoms of disease. This scale will be scored as a static assessment; i.e., without regard to a previous assessment. To have IGA success, one must have a designation of 'clear' or 'almost clear' and exhibit a two-point improvement from baseline. Hence, if a patient has 'mild' disease at baseline, he/she must reach 'clear'. If a patient has 'moderate' disease at baseline, he/she must reach 'almost clear'. And, if a patient is classified as 'severe' at baseline, he/she must still reach 'almost clear', even though that requires a three-point improvement.

Training will be mandatory for trial investigators involved in this assessment

Itch Numeric Rating Scale—The Itch NRS is a self-administered patient reported outcome questionnaire that is completed during protocol specified clinic visits. Subjects indicate itch severity by circling the integer that best describes the worst level of itching due to psoriasis in the past 24 h on an 11-point scale anchored at 0, representing 'no itching' and 10, representing 'worst itch imaginable'.

Dermatology Life Quality Index (DLQI)—DLQI is the dermatology-specific quality of life measure used for psoriatic population. The 10-item questionnaire assesses participant health-related quality of life (daily activities, personal relationships, symptoms and feelings, leisure, work and school, and treatment). The DLQI questions are rated by the participant as 0 (not at all/not relevant) to 3 (very much) with a total score range of 0 (best) to 30 (worst); higher scores indicate poor quality of life.

Patient's Global Assessment (PtGA)—The PtGA asks the participant to evaluate the overall cutaneous disease at that point in time on a single item, 5-point scale (0=clear; 1=almost clear; 2=mild; 3=moderate; 4=severe).

Coronary artery perivascular fat attenuation index (FAI)—measured by CT angiography.

TABLE 5

Schedule of Assessments

| Study Period | SCRN | Baseline | Treatment Phase | | | | | | | |
|---|---|---|---|---|---|---|---|---|---|---|
| Visit | | 1 | 2 | 3 | 4 | 5 | 6 | 7 | 8 | 9 |
| Study Day $^{a,b}$ | −30 to −1 | 1 | $14^b$ | $28^b$ | $42^b$ | $56^b$ | $70^b$ | $84^{\ b}$ | $98^{\ b}$ | $112^{\ b}$ |
| Study Week | | | 2 | 4 | 6 | 8 | 10 | 12 | 14 | 16 |
| Informed Consent Form | X | | | | | | | | | |
| Inclusion/Exclusion Criteria | X | X | | | | | | | | |
| Randomization | | X | | | | | | | | |
| Demographic Data | X | | | | | | | | | |
| Medical History | X | | | | | | | | | |
| Incl. Hx of Psoriatic Arthritis | | | | | | | | | | |
| Laboratory Evaluation$^c$ | X | X | X | | X | | | X | | X |
| Pregnancy Test$^d$ | X | X | | | X | | | | | X |
| Vital Signs $^e$ | $X^e$ | $X^e$ | $X^e$ | $X^e$ | $X^e$ | $X^e$ | $X^e$ | $X^e$ | $X^e$ | $X^e$ |
| Triplicate 12-Lead ECG$^f$ | X | X | X | | X | | | X | | X |
| Dermatologic Examination$^g$ | $X^g$ | $X^g$ | | X | | X | | X | | X |
| Digital pictures of neck, trunk and limbs (selected sites) | | X | X | | X | | X | | | |
| CCTA | X | | | | | | | | | |
| Physical Examination | X | X | | | | | | | | |
| PASI | X | X | | X | | X | | X | | X |
| BSA | X | X | | | | | | | | X |
| sIGA$^g$ | $X^g$ | $X^g$ | | X | | X | | X | | X |
| PtGA | X | X | | | | | | | | X |
| INRS | | X | | X | | X | | X | | X |
| DLQI | | X | | | | | | | | X |
| Psoriatic Arthritis Questionnaire | | X | | | | | | | | |
| Study Drug Administration | | X | — | X | — | X | — | X | — | X |
| Study Drug Accountability | | X | X | X | X | X | X | X | X | X |
| Adverse Events | X | X | X | X | X | X | X | X | X | X |
| Concomitant Medications | X | X | X | X | X | X | X | X | X | X |

PK=Pharmacokinetic; ECG=electrocardiogram; ET=early termination; F/U=Follow-up; Psoriasis Area and Severity Index—PASI; BSA=percent body surface affected by psoriasis; Static Investigator's Global Assessment (sIGA); Patient's Global Assessment (PtGA); Clinic-Based Itch Numerical Rating Scale (INRS); Dermatology Life Quality Index (DLQI); Coronary computed tomographic angiography (CCTA)

$^a$Unscheduled visits may be performed at any time for safety reasons and/or for any other reason. Safety labs, EKGs and physical examinations and other assessments may be performed at the discretion of the investigator.

$^b$Visit should occur within ±3 days.

$^c$Includes hematology and coagulation testing, hsCRP, SMA25 (Serum—amylase, Comprehensive Metabolic Profile (CMP) (includes eGFR): (A:G ratio; albumin, serum; alkaline phosphatase, serum; ALT (SGPT); AST (SGOT); bilirubin, total; BUN; BUN:creatinine ratio; calcium, serum; carbon dioxide, total; chloride, serum; creatinine, serum; globulin, total; glucose, serum; potassium, serum; protein, total, serum; sodium, serum.) Creatine Kinase (CK), Total, Serum Gamma Glutamyl Transpeptidase (GGT); Lactic Acid Dehydrogenase (LD); Lactic Acid, Plasma Lipid Panel: Cholesterol, total; high-density lipoprotein (HDL) cholesterol; low-density lipoprotein (LDL) cholesterol (calculation); triglycerides; very low-density lipoprotein (VLDL), Lipoprotein(a) oxLDL and oxHDL; Magnesium, Serum; Phosphorus, Serum; Uric Acid, Serum Also, a urinalysis at all indicated visits. A urine drug screen will also be performed at Screening. Hepatitis panel at screen only, An FSH screen will be performed at Screening in postmenopausal women. A Mantoux tuberculin skin test is performed at screen only (for subjects that have had the Bacille Calmette-Guerin (BCG) vaccine an Interferon-gamma Release Assay (IGRA) can be offered).

$^d$For women of child bearing potential. A serum pregnancy test at Screening (central laboratory) and urine pregnancy test at all other visits noted (clinical site).

$^e$Includes supine (at least 5 minutes) for blood pressure, pulse rate, respiratory rate, body temperature, and standing (after 1 and 3 minutes) for blood pressure and pulse rate. Height will be measured once at Screening. Body weight will be measured at visits 1, 4, 7 and 9 and recorded in pounds (lbs) and BMI entered in the CRF $^f$Triplicate electrocardiograms will be recorded after the subject has rested quietly for 5 minutes in a supine position.

$^g$At screening and pre-dose baseline dermatologic examination must show the presence of moderate Plaque Psoriasis characterized by raised, inflamed lesions covered with a silvery white scale. The scale may be scraped away to reveal inflamed skin beneath.

TABLE 6

Schedule of Assessments

| Study Period | Treatment Phase | | | | | | | | Follow Up |
|---|---|---|---|---|---|---|---|---|---|
| Visit | 10 | 11 | 12 | 13 | 14 | 15 | 16 | 17 | 19/ET | 20/FU |
| Study Week $^{a,b}$ | 20 | $24^b$ | $28^b$ | $32^b$ | $36^b$ | $40^b$ | $44^b$ | $48^b$ | $52^b$ | $54^b$ |

TABLE 6-continued

Schedule of Assessments

| Study Period | Treatment Phase | | | | | | | | | Follow Up |
|---|---|---|---|---|---|---|---|---|---|---|
| Laboratory Evaluation[c] | X | X | | X | | | X | | X | X |
| Pregnancy Test[d] | | | | X | | | | | | X |
| Vital Signs[e] | X[e] | X[e] | X[e] | X[e] | X[e] | X[e] | X[e] | X[e] | X[e] | X[e] |
| Triplicate 12-Lead ECG[f] | X | X | | X | | X | | X | X | |
| Dermatologic Examination | X | X | X | X | X | X | X | X | X | |
| Digital pictures of neck, trunk and limbs (selected sites) | | X | | X | | X | | | X | |
| CCTA | | | | | | | | | X | |
| Physical Examination | | | X | | X | | | | X | |
| PASI | X | X | X | X | X | X | X | X | X | |
| sIGA | | | X | | X | | | | X | |
| PtGA | | | | | X | | | | X | |
| BSA | | | | | | | | | X | |
| INRS | X | X | X | X | X | X | X | X | X | |
| DLQI | | | | | | | | | X | |
| Psoriatic Arthritis Questionnaire | | | | | | | | | X | |
| Digital Photograph (selected sites) | | | | | | | | | X | |
| Study Drug Administration | X | X | X | X | X | X | X | X | — | |
| Study Drug Accountability | X | X | X | X | X | X | X | X | X | |
| Adverse Events | X | X | X | X | X | X | X | X | X | |
| Concomitant Medications | X | X | X | X | X | X | X | X | X | |

PK=Pharmacokinetic; ECG=electrocardiogram; ET=early termination; F/U=Follow-up; Psoriasis Area and Severity Index—PASI; BSA=percent body surface affected by psoriasis; Static Investigator's Global Assessment (sIGA); Patient's Global Assessment (PtGA); Investigator Global Assessment (sIGA); Clinic-Based Itch Numerical Rating Scale (INRS); Dermatology Life Quality Index (DLQI); Coronary computed tomographic angiography (CCTA)

[a]Unscheduled visits may be performed at any time for safety reasons and/or for any other reason. Safety labs, EKGs and physical examinations and other assessments may be performed at the discretion of the investigator.

[b]Visit should occur within ±3 days.

[c]Includes hematology and coagulation testing, hsCRP; SMA25 (Serum-amylase, Comprehensive Metabolic Profile (CMP) (includes eGFR): (A:G ratio; albumin, serum; alkaline phosphatase, serum; ALT (SGPT); AST (SGOT); bilirubin, total; BUN; BUN:creatinine ratio; calcium, serum; carbon dioxide, total; chloride, serum; creatinine, serum; globulin, total; glucose, serum; potassium, serum; protein, total, serum; sodium, serum.) Creatine Kinase (CK), Total, Serum Gamma Glutamyl Transpeptidase (GGT); Lactic Acid Dehydrogenase (LD); Lactic Acid, Plasma Lipid Panel: Cholesterol, total; high-density lipoprotein (HDL) cholesterol; low-density lipoprotein (LDL) cholesterol (calculation); triglycerides; very low-density lipoprotein (VLDL) cholesterol (calculation); Lipoprotein(a), Magnesium, Serum; Phosphorus, Serum; Uric Acid, Serum Also, a urinalysis at all indicated visits. A urine drug screen will also be performed at Screening. Hepatitis panel at screen only, An FSH screen will be performed at Screening in postmenopausal women. A Mantoux tuberculin skin test is performed at screen only (for subjects that have had the Bacille Calmette-Guerin (BCG) vaccine an Interferon-gamma Release Assay (IGRA) can be offered).

[d]For women of child bearing potential. A serum pregnancy test at Screening (central laboratory) and urine pregnancy test at all other visits noted (clinical site).

[e]Includes supine (at least 5 minutes) for blood pressure, pulse rate, respiratory rate, body temperature, and standing (after 1 and 3 minutes) for blood pressure and pulse rate. Height will be measured once at Screening. Body weight will be measured at visits 10, 14, 19 and 20 and recorded in pounds (lbs) and BMI entered in the CRF

[f]Triplicate electrocardiograms will be recorded after the subject has rested quietly for 5 minutes in a supine position.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method for treating, reducing the severity of, slowing progression of, or inhibiting psoriasis or psoriatic arthritis in a subject in need thereof, comprising:
administering to the subject an effective amount of an antibody or antibody fragment capable of binding to a fragment of apolipoprotein B100 (ApoB100),
wherein the fragment of ApoB100 comprises an amino acid sequence of SEQ ID NO: 1, and wherein the antibody comprises an HCDR 1 having the sequence of SEQ ID NO: 2, an HCDR 2 having the sequence of SEQ ID NO: 3, and an HCDR 3 having the sequence of SEQ ID NO: 4, a light chain determining region 1 having a sequence of SEQ ID NO: 5, an LCDR 2 having a sequence of SEQ ID NO: 6, and an LCDR 3 having a sequence of SEQ ID NO: 7.

2. The method of claim 1, wherein the fragment of ApoB100 is an aldehyde derivative.

3. The method of claim 1, wherein the antibody comprises the variable heavy region ($V_H$) of SEQ ID NO: 8, the variable light region ($V_L$) of SEQ ID NO: 9, or both.

4. The method of claim 3, wherein the antibody comprises the heavy chain of SEQ ID NO: 10, the light chain of SEQ ID NO: 11, or both.

5. The method of claim 1, wherein the antibody is orticumab.

6. The method of claim 1, wherein the psoriasis is plaque psoriasis.

7. The method of claim 6, wherein the subject does not have a non-plaque form of psoriasis, wherein the non-plaque form comprises erythrodermic, guttate or pustular psoriasis.

8. The method of claim 1, wherein the subject is a human, the antibody is orticumab, and orticumab is administered subcutaneously at a dose of about 330 mg/month for about 3, 4, 5, 6, 7, 8, 9, 10, 11 or 12 months.

9. The method of claim 1, wherein the antibody is orticumab and is administered intravenously at an initial dose of at least 5 mg/kg, followed by a plurality of subsequent doses, each at least 2 mg/kg/week, at least 2.5 mg/kg/two weeks, or at least 6 mg/kg/month.

10. The method of claim 1, wherein the antibody or antibody fragment is administered at 1-10 µg/kg, 10-100 µg/kg, 100-500 µg/kg, 200-500 µg/kg, 300-500 µg/kg, 400-500 µg/kg, 1-5 mg/kg, 5-10 mg/kg, 10-15 mg/kg, 15-20 mg/kg, 20-25 mg/kg, 25-50 mg/kg, or 50-75 mg/kg.

11. The method of claim 1, wherein the subject further exhibits symptoms of atherosclerosis before the administration, and after the administration the subject has reduced plaque volume.

12. The method of claim 1, further comprising administering a topical corticosteroid, a vitamin D analogue, a topical retinoid, a keratolytic agent, coal tar, ultraviolet A, ultraviolet B, an anti-tumor necrotic factor (TNF) antibody, an anti-interleukin (IL)-12/23 antibody, an anti-IL-23 antibody, an anti-IL-17 antibody, or a combination thereof, wherein the vitamin D analogue comprises calcitriol, calcipotriene, maxacalcitol or tacalcitol.

13. The method of claim 1, wherein the subject exhibits symptoms of psoriasis or psoriatic arthritis and is refractory to UVA therapy, UVB therapy, a topical steroid, or a combination thereof.

14. The method of claim 1, wherein the subject has an elevated amount of tumor necrosis factor-alpha (TNFα), interleukin 6 (IL-6), C-reactive protein (CRP), or a combination thereof, compared to a control subject free of psoriasis or psoriatic arthritis.

15. The method of claim 1, further comprising selecting a subject exhibiting symptoms of psoriasis or psoriatic arthritis or a subject who has been diagnosed with psoriasis or psoriatic arthritis.

16. A method for passive immunization of a subject, wherein a therapeutically effective amount of an antibody or antibody fragment capable of binding to a fragment of ApoB100 is administered for treatment of psoriasis or psoriatic arthritis, wherein the fragment of ApoB100 is SEQ ID NO: 1, and wherein the antibody comprises an HCDR 1 having the sequence of SEQ ID NO: 2, an HCDR 2 having the sequence of SEQ ID NO: 3, and an HCDR 3 having the sequence of SEQ ID NO: 4, an LCDR 1 having a sequence of SEQ ID NO: 5, an LCDR 2 having a sequence of SEQ ID NO: 6, and an LCDR 3 having a sequence of SEQ ID NO: 7.

17. The method of claim 16, wherein the antibody comprises the variable heavy region ($V_H$) of SEQ ID NO: 8, the variable light region ($V_L$) of SEQ ID NO: 9, or both.

18. The method of claim 16, wherein the antibody comprises the heavy chain of SEQ ID NO: 10, the light chain of SEQ ID NO: 11, or both.

19. The method of claim 16, wherein the antibody is orticumab, which is administered subcutaneously at a dose of about 330 mg/month for about 3, 4, 5, 6, 7, 8, 9, 10, 11 or 12 months.

20. The method of claim 16, wherein the subject is diagnosed with psoriasis or psoriatic arthritis and characterized by an elevated amount of tumor necrosis factor-alpha (TNFα), interleukin 6 (IL-6), C-reactive protein (CRP), or a combination thereof, compared to a subject free of psoriasis or psoriatic arthritis.

\* \* \* \* \*